United States Patent
Ljungmann et al.

(10) Patent No.: US 9,557,249 B2
(45) Date of Patent: Jan. 31, 2017

(54) INSTRUMENT, APPARATUSES AND DEVICES FOR PRETREATING CELLS

(71) Applicant: Instrunor AS, Nesoddtangen (NO)

(72) Inventors: Oystein Helge Ljungmann, Siggerud (NO); Torstein Ljungmann, Nesoddtangen (NO)

(73) Assignee: INSTRUNOR AS, Bjornemyr (NO)

( * ) Notice: Subject to any disclaimer, the term of this patent is extended or adjusted under 35 U.S.C. 154(b) by 395 days.

(21) Appl. No.: 13/774,147

(22) Filed: Feb. 22, 2013

(65) Prior Publication Data

US 2013/0224851 A1    Aug. 29, 2013

Related U.S. Application Data

(63) Continuation-in-part of application No. PCT/NO2012/050031, filed on Feb. 24, 2012.

(51) Int. Cl.
| | |
|---|---|
| *G01N 1/31* | (2006.01) |
| *B04B 5/04* | (2006.01) |
| *G01N 35/02* | (2006.01) |
| *G01N 35/00* | (2006.01) |
| *G01N 35/04* | (2006.01) |

(52) U.S. Cl.
CPC .............. *G01N 1/31* (2013.01); *B04B 5/0421* (2013.01); *G01N 35/025* (2013.01); *G01N 2035/00504* (2013.01); *G01N 2035/00524* (2013.01); *G01N 2035/0441* (2013.01); *G01N 2035/0444* (2013.01); *G01N 2035/0446* (2013.01); *G01N 2035/0449* (2013.01)

(58) Field of Classification Search
None
See application file for complete search history.

(56) References Cited

U.S. PATENT DOCUMENTS

| | | | |
|---|---|---|---|
| 4,054,415 A | 10/1977 | Seligson et al. | |
| 4,208,484 A | 6/1980 | Sogi et al. | |
| 5,030,554 A | 7/1991 | Quintana et al. | |
| 5,045,047 A | 9/1991 | Hutchins et al. | |
| 5,167,926 A | 12/1992 | Kimura et al. | |
| 5,472,669 A | 12/1995 | Miki et al. | |
| 2002/0132354 A1* | 9/2002 | Downs | B04B 5/0414 436/45 |

(Continued)

FOREIGN PATENT DOCUMENTS

| | | |
|---|---|---|
| DE | 88 04 938.8 U1 | 5/1988 |
| EP | 0 418 026 A2 | 3/1991 |

(Continued)

OTHER PUBLICATIONS

International Search Report and Written Opinion of the International Searching Authority issued Jan. 16, 2013 in corresponding International Application No. PCT/NO2012/050031.

*Primary Examiner* — Jill Warden
*Assistant Examiner* — Julie Tavares
(74) *Attorney, Agent, or Firm* — Wenderoth, Lind & Ponack, L.L.P.

(57) ABSTRACT

A system and apparatuses or devices capable of automatically performing processes of cell treatment preparatory to flow cytometry and similar cytological studies in a fully automated and streamlined manner are provided. The system and apparatuses or devices are adapted for preparation and (pre)processing of cell samples, e.g., blood and/or bone marrow samples.

42 Claims, 27 Drawing Sheets

(56) References Cited

U.S. PATENT DOCUMENTS

| | | | |
|---|---|---|---|
| 2003/0030783 A1 | 2/2003 | Roche et al. | |
| 2003/0091473 A1 | 5/2003 | Downs et al. | |
| 2003/0138967 A1 | 7/2003 | Hall et al. | |
| 2005/0123445 A1 | 6/2005 | Blecka et al. | |
| 2006/0203226 A1 | 9/2006 | Roche et al. | |
| 2007/0184546 A1 | 8/2007 | Farrelly et al. | |
| 2009/0068062 A1 | 3/2009 | Jafari et al. | |
| 2009/0142846 A1 | 6/2009 | Crenshaw et al. | |
| 2010/0105074 A1 | 4/2010 | Covey et al. | |
| 2010/0261595 A1* | 10/2010 | Schaefer ............... | B04B 7/08 494/20 |
| 2011/0017238 A1 | 1/2011 | Kuroda | |

FOREIGN PATENT DOCUMENTS

| | | |
|---|---|---|
| EP | 0 557 828 | 9/1993 |
| EP | 0 628 822 A2 | 12/1994 |
| EP | 0 645 631 B1 | 11/2001 |
| EP | 2 261 632 | 12/2010 |
| EP | 2 407 791 A1 | 1/2012 |
| JP | 52-84792 | 7/1977 |
| JP | 4-34366 | 2/1992 |
| JP | 4-242168 | 8/1992 |
| JP | 5-232122 | 9/1993 |
| JP | 10-267938 | 10/1998 |
| JP | 2003-83979 | 3/2003 |
| JP | 2003-531381 | 10/2003 |
| JP | 2006-158335 | 6/2006 |
| JP | 2007-524831 | 8/2007 |
| JP | 2008-164580 | 7/2008 |
| JP | 2009-270845 | 11/2009 |
| JP | 2010-133727 | 6/2010 |
| WO | 01/79857 | 10/2001 |
| WO | 03/062796 | 7/2003 |
| WO | 2009/122999 | 10/2009 |
| WO | 2009/150632 A2 | 12/2009 |
| WO | 2010/110265 A1 | 9/2010 |
| WO | 2012/012779 A1 | 1/2012 |

* cited by examiner

INSTRUMENT, APPARATUSES AND DEVICES FOR PRETREATING CELLS

This application is a Continuation-In-Part of International Application No. PCT/NO2012/050031, filed Feb. 24, 2012, the contents of which is incorporated herein by reference in its entirety.

TECHNICAL FIELD

The present invention teaches a fully automated instrument and its belonging units or devices, used therein or alone, for preparing cell samples that are to be used thereafter in e.g. flow cytometry analysis. The preparation procedure can comprise some of the following steps: staining, lysing and fixation of cells.

BACKGROUND OF THE INVENTION

Flow cytometry represents one of the essential tools employed in such fields as cytologic biology, cellular immunochemistry, and cytodiagnosis for cancer detection. Essentially, it aims at the classification of cells according to their sizes, types, contents of intracellular components, and like characteristics. Flow cytometry involves the pigmentation of cells with fluorescent dyes. The pigmented cells are caused to individually fluoresce under laser beam irradiation while flowing through slender tubing. The intensities of fluorescence of the individual cells are measured for the determination of their sizes, relative amounts of DNA (deoxyribonucleic acid), etc. Flow cytometry analysis can identify and enumerate lymphocyte subsets in human cells in suspension.

One usage of the system, apparatuses and devices according to the present invention can be found in immunology and pathology laboratories at hospitals all over the world.

Conventionally, such cell pretreatment has been mostly performed manually at the cost of much time and labor. Manual pretreatment is also undesirable by reasons of unavoidable human errors and the non-uniformity of operations from one individual operator to another. The advent of an apparatus capable of full automation of cell pretreatment has thus been long awaited by the cytologists for the elimination of human toil and for gaining stability and constancy in the operations involved. No such system or apparatus is known, because of the complexities of the processes of cell pretreatment. However, there are several companies trying to partially automate some of the processes.

Becton-Dickinson (BD) with its BD Facs Lyse Wash Assistant (for automatic lysing, washing and centrifuging) and Beckmann Coulter with its TQ Prep Workstation (for automatic lysing procedure), the PrepPlus 2 Workstation (for pipetting of reagents, patient samples, controls and fluorospheres into daughter tubes), and the Antibody Cocktail Preparation Workstation (for cocktail mixing) offer complementary automation to the manual process.

The BD Facs Lyse Wash Assistant does not pipette reagents or patient samples. The centrifuge solution is based on a single vial (tube) centrifuge, where the vial rotates around its own axe. The inconvenience with that centrifuge solution is that the cells in the sample won't gather in the bottom of the vial, but on the walls. One lab engineer interviewed mentioned that there is a problem with losing too many cells in this process.

EP 0 645 631 B1, assigned to Becton Dickinson, describes an automated system for preparing samples and for loading the samples to an analyzer, wherein the system includes a sample carousel which mixes and indexes a plurality of sample tubes to a sample aspiration station.

Beckman Coulter offers several instruments in order to automate the complete manual procedure. The unfortunate outcome of using that strategy is that the automated process will still include several manual activities after buying these instruments. After pipetting patient samples and reagents in the PrepPlus 2 Workstation, the sample(s) must be manually moved to the TQ Prep Workstation for lysing procedure. The FP1000 Cell Preparation System is also a part of the Beckman Coulter family and is being used for lysing solutions.

EP 1 468 266 A1, assigned to Beckman Coulter, relates to an adjustably controllable environment containment system for a flow cytometer to protect both the particles being processed by the flow cytometer from contamination by both biological and non-biological materials and to protect persons using the flow cytometer from being exposed to the particles being processed and the chemistry utilized in the processing of such particles.

JP 2010133727, assigned to Beckman Coulter, regards a cleaning mechanism for cleaning an approximately cylindrical dispensation nozzle.

US 2011/017238 A1, assigned to Beckman Coulter, teaches a nozzle cleaning method and a nozzle cleaning device which allow to surely perform cleaning of a dispensing nozzle and which allow reduction in cleaning time. For this purpose, a nozzle cleaning method for cleaning a dispensing nozzle for suctioning and discharging a liquid includes: a first cleaning step in which, after termination of dispensing, an inner wall surface of the dispensing nozzle is cleaned in an upper portion of a storage tank overflowed with a cleaning liquid by discharging a liquid for preload; and a second cleaning step in which at least an outer wall surface is cleaned by lowering and immersing the dispensing nozzle into the storage tank overflowed with the cleaning liquid.

EP 2 407 791 A1, assigned to Beckman Coulter, relates to an analyzer comprising: a reading section for storing or obtaining specimen information including a sample type of a specimen, and specimen container information; a liquid level detecting section for detecting a liquid level and/or an interface of the specimen; a dispensing apparatus for dispensing a specimen; a washing apparatus for washing a dispensing probe; a calculating section for calculating a contamination adhering range of an external wall surface of the dispensing probe, based on the sample type, specimen suction-position and specimen container information stored or obtained by the reading section, as well as liquid level and/or interface information of the specimen detected by the liquid level detecting section; and a washing control section for controlling a washing range based on the contamination adhering range.

WO 2010/110265 A1, assigned to Beckman Coulter, describes dispenser comprising a storage section for storing a voltage correction coefficient for each specimen type and voltage correction coefficients based on the type of containers which contain specimens, an information reader for acquiring specimen information and container information, a calculating section for calculating a threshold voltage on the basis of the voltage correction coefficient of a specimen and the voltage correction coefficient of a container, which have been extracted from the storage section, and a determination section for determining to be liquid-level detection when the signal received by a dispensing probe outputs the threshold voltage for a predetermined period or longer.

U.S. Pat. No. 5,030,554, assigned to Beckman Coulter, discloses a method for rapid preparation of a whole blood sample for photo-optical analysis.

EP 0 418 026 A2 refers to an apparatus for pretreating cells for flow cytometry.

WO 2009/150632 A2 discloses an apparatus for preparing controlled amounts of liquid for cytometry, which apparatus comprises a sampler having: motion imparting means for moving a main tray with one or more tubes thereon, each containing a controlled amount of liquid; a support and moving unit for supporting and moving a syringe that transfers preparation liquids into the tubes; a motion imparting mechanism for moving the piston of the syringe. The apparatus further comprises a centrifuge located beside the sampler and having an access opening for receiving the tubes, for selective removal of residues to be discarded from the controlled amounts of liquid. Furthermore, the sampler comprises a motorized gripping mechanism disposed in the support and moving unit and coaxial with the syringe, the support and moving unit being movable to allow the tubes to be carried from the main tray to the centrifuge, and vice versa.

EP 0 628 822 A2 teaches a blood analysis system or instrument, generally, including an incubator station, a sample and reagent holding station, a pipette assembly, a centrifuge, an analysis station, and a transport assembly. Generally, the incubation station holds containers while reagents and fluids are being dispensed in those containers, and, if desired, for incubating the containers. The sample and reagent holding station holds samples and a plurality of reagents, and the pipette assembly transfers fluids from that sample and reagent holding station to containers in the incubation station. The centrifuge is provided for centrifuging the container, and the analysis station is provided to analyze the containers, optically to identify reactions therein. The transport assembly carries the containers between the incubator station, the centrifuge, and the analysis station. Preferably, the pipette assembly is automatically operated to draw fluids and preselected reagents from the sample and reagent holding station, and to dispense fluids into the containers held in the incubation station to produce predetermined solutions therein. Also, the transport subassembly is automatically operated to carry containers from the incubator station to the centrifuge after the predetermined solutions have been produced in the containers, and then to carry the containers from the centrifuge to the analysis station.

None of the previously mentioned prior art products teaches a fully automated system as well as its sufficiently developed components/units/devices therein, where the system and its different components/devices are being adapted for cooperating and working together in a streamlined and seamless manner and for preparing of cells that are to be thereafter used in flow cytometry analysis.

One of the problems left unsolved in the art of flow cytometry is how to expedite the complete process of pretreating cells to be studied. Such pretreatment consists of many steps to be followed strictly in a prescribed order. Among the steps are introduction of reagents into cell samples within sample tubes, centrifugal treatment of the sample-reagent mixtures, removal of the unnecessary liquid tops from the sample tubes, staining of the cells with a fluorescent dye, and filtration of the samples. The actual process is much more complex.

One aspect of the present invention is to provide a system and improved apparatuses/devices for a fully automated and streamlined, as well as more effective/efficient, preparation or pretreatment procedure of cells preparatory to their flow cytometric or similar cytological studies.

It is also an aspect of the present invention is to provide for reducing or eliminating any possibility for contamination of cell sample(s) being prepared or pretreated.

Another aspect of the present invention is to provide for reducing the loss of too many cells during the preparation or pretreatment procedure or process.

Yet another aspect of the present invention is to provide for full control of antibody and reagent usage, as well as minimizing faulty on analysis due to manual mistakes when e.g. staining.

SUMMARY OF THE INVENTION

The present invention seeks to provide a system and apparatuses/devices capable of automatically performing the processes of cell treatment preparatory to flow cytometry and similar cytological studies in a fully automated and streamlined manner. The system and apparatuses/devices are being adapted for preparation and (pre)processing of blood and/or bone marrow samples.

The present invention provides an instrument or system for automated preparing or pretreating of a cell sample or samples ahead of flow cytometry analysis, comprising a main test sample rack arrangement or means for a certain number of sample containers; a carousel/centrifuge arrangement or means comprising several holder means for one or several secondary sample containers; an antibody/stabilizer container and cooler arrangement or means for a predetermined number of stabilizes or the like, such as at least one of the following: antibodies, reagents, cocktail mixtures, and providing for sustaining a desired temperature range therein; a robot arrangement or means arranged for mechanically or physically serving the system; and a computer means comprising at least one CPU and provided for controlling and/or operating of all components, apparatuses or devices of the system in order to achieve full automation of the entire cell pretreating process.

The system or instrument can further comprise a reagent rack arrangement adapted to accommodate one or more reagent bottles.

The main test sample rack arrangement can comprise, in its proximity, means for automated removing of and/or putting on one or more sample container caps. The main test sample rack arrangement can further comprise an additional sample container holding means for holding one or more sample containers of a different type.

The robot arrangement or means comprises three axes (x,y,z) and together with its elements/components can allow and/or provide for movement(s) in all directions within the x,y,z or 3D area or space of the system. The robot arrangement can further comprise at least one arm arrangement and at least one needle or syringe arrangement or means comprising at least one needle or cannula and at least one syringe having a plunger. The plunger therein can be operated by at least one motor driven mechanism.

Said at least one needle or syringe arrangement or means can comprise two syringes placed substantially vertically and parallel with each other, where one syringe is adapted for small volumes of liquid(s) within the microliter (µl) range and the other syringe is adapted for big or large volumes of liquid(s) within the milliliter (ml) range.

Said system or instrument can further comprise a cleansing or rinsing arrangement or station, where said at least one syringe of the needle or syringe arrangement can be cleansed or rinsed with the help of at least one cleansing or rinsing fluid or liquid or solution and/or chemical.

The system or instrument can further comprise a waste station. The exceeding liquid wasting means can be connected to said waste station. The waste station can have pumping means and be adapted for collecting waste fluid(s), liquid(s), stabilizer(s), reagent(s), antibodies and/or sample(s).

The computer means can comprise output interface and input interface, such as at least one of the following: a screen or display, a keyboard, and a keyset of button(s). The computer means can further comprise storage or memory means.

The system can further comprise means for wired and/or wireless and/or Bluetooth® communication with external devices.

The system or instrument can further comprise a housing and a lid. Said housing and lid can be made of light reductive and/or non-transparent material, wherein, when the lid is in a closed position with respect to the housing, both the lid and housing can be arranged to provide for incubation and/or lysing in the dark and/or excluding damaging UV-rays of the processed or pretreated cell samples The carousel/centrifuge arrangement or means in the instrument can comprise a motor drive arrangement or means allowing for movement or centrifuging in clockwise and/or counterclockwise direction. The carousel/centrifuge arrangement or means can be arranged for functioning as a centrifuge and for applying "swinging bucket" principle. The carousel/centrifuge arrangement or means can further comprise a titrating or shaking arrangement driven by a motor driven arrangement in order to shake and/or vortex the contents of said secondary sample container in the holder means. The titrating or shaking arrangement can be adapted to lift up the holder means in order to empty or pour out exceeding liquid within said secondary sample container into exceeding liquid wasting means further connectable to the waste station.

The carousel/centrifuge arrangement therein can be made detachable.

The system or instrument can further comprise a cell density detection means for detecting the cell density of the cells in a certain main or mother test tube or sample container. The cell density detection means can comprise an optical fiber means arranged to send or emit light through the cells being on or into a suitable transparent plate/slide or container, and a light receiving or detection means arranged on the opposite side or end thereof and adapted to receive the emitted light for further processing and/or estimating of the cell density.

The system can further comprise a hose or pipe arrangement connecting or coupling different container(s) and/or chamber(s) and/or bottle(s) therein.

The system can further comprise a fluid level measuring means for measuring and/or controlling/checking of the fluid level in a container or chamber arranged in at least one of the following: the antibody and cooler arrangement; the reagent rack arrangement with said at least one bottle; cleansing or rinsing arrangement; and the main test sample rack arrangement, where the fluid level measuring means is arranged in an electronic circuit with at least one of the needle(s) of the needle or syringe arrangement or means, so that the electronic circuit registers when the needle tip touches the fluid surface in the container or chamber that is to be checked, and, based on the liquid or fluid height from the bottom of the container or chamber to the fluid surface therein and in the vertical or z axis direction, the remaining fluid volume or amount is being calculated.

The antibody/stabilizer container and cooler arrangement or means can comprise a housing and a cover having a number of holes placed over a plurality of specially designed tubes or containers adapted for antibodies/stabilizers/reagents, or ready mixed cocktails, etc. and/or a number of bottles or containers, of at least one type, from at least one antibody fluid supplier, where each hole is adapted for a needle to come therethrough and further into the tube or container and/or supplier bottle or container thereunder in order to suck up liquid therefrom without removing the cover, thus avoiding temperature changes within said antibody/stabilizer container and cooler arrangement or means. The antibody/stabilizer container and cooler arrangement can further comprise a cooling means comprising at least one inlet circulation fan, at least one outlet circulation fan, and a heat sink having a number of Peltier elements, for securing the sustainment of the desired temperature range therein. The antibody/stabilizer container and cooler arrangement can further comprise at least two cartridges or cassettes for a plurality of specially designed tubes or containers for antibodies/stabilizers/reagents, or ready mixed cocktails, etc. and/or for a number of bottles or containers, of at least one type, from at least one antibody fluid supplier, wherein at least one of said cartridges or cassettes is made detachable.

As mentioned above, the invention teaches an antibody/stabilizer container and cooler arrangement or means being arranged for a predetermined number of stabilizes or the like, such as at least one of the following: antibodies, reagents, cocktail mixtures, wherein said antibody/stabilizer container and cooler arrangement or means is provided for sustaining a desired temperature range therein. The antibody/stabilizer container and cooler arrangement can further comprise a housing and a cover having a number of holes placed over a plurality of specially designed tubes or containers adapted for antibodies/stabilizers/reagents, or ready mixed cocktails, etc. and/or a number of bottles or containers, of at least one type, from at least one antibody fluid supplier, where each hole is adapted for a needle to come therethrough and further into the tube or container and/or supplier bottle or container thereunder in order to suck up liquid therefrom without removing the cover, thus avoiding temperature changes within said antibody/stabilizer container and cooler arrangement or means. The antibody/stabilizer container and cooler arrangement can further comprise a cooling means comprising at least one inlet circulation fan, at least one outlet circulation fan, and a heat sink having a number of Peltier elements, for securing the sustainment of the desired temperature range therein. The antibody/stabilizer container and cooler arrangement can further comprise at least two cartridges or cassettes for a plurality of specially designed tubes or containers for antibodies/stabilizers/reagents, or ready mixed cocktails, etc. and/or for a number of bottles or containers, of at least one type, from at least one antibody fluid supplier, wherein at least one of said cartridges or cassettes is made detachable. The antibody/stabilizer container and cooler arrangement can be adapted for use in the system or instrument of the present invention.

As mentioned above, the invention teaches a carousel/centrifuge arrangement or means comprising several holder means for one or several sample containers, wherein said carousel/centrifuge arrangement or means is arranged for functioning as a centrifuge and for applying "swinging bucket" principle. The carousel/centrifuge arrangement or means can further comprise a motor drive arrangement or means allowing for movement or centrifuging in clockwise and/or counterclockwise direction. The carousel/centrifuge arrangement or means according can further comprise a titrating or shaking arrangement driven by a motor driven arrangement in order to shake and/or vortex the contents of said sample container in the holder means. The titrating or shaking arrangement therein is adapted to lift up the holder means in order to empty or pour out exceeding liquid within said sample container into exceeding liquid wasting means. The exceeding liquid wasting means can further be connectable to a waste station. The carousel/centrifuge arrangement or means can further comprise a cell density detection means for detecting the cell density of the cells in a certain main or mother test tube or sample container. The cell density detection means therein can comprise an optical fiber means arranged to send or emit light through the cells being on or into a suitable transparent plate/slide or container, and a light receiving or detection means arranged on the opposite side or end thereof and adapted to receive the emitted light for further processing and/or estimating of the cell density. The carousel/centrifuge arrangement or means can in addition be arranged to be detachable. The carousel/centrifuge arrangement or means can be adapted for use in the system or instrument of the present invention.

The motor drive arrangement of the carousel/centrifuge arrangement (adapted for the instrument) can further be arranged for centrifuging with different speeds.

The carousel/centrifuge arrangement or means (adapted for the instrument) can further comprise a housing and a lid. Said housing and lid can be made light reductive and/or of non-transparent material, wherein, when the lid is in a closed position with respect to the housing, both the lid and housing can be arranged to provide for incubation and/or lysing in the dark and/or excluding damaging UV-rays of the processed or pretreated cell samples.

The present invention provides a software product stored on a readable and/or recordable media that is provided for control and/or management and/or operation of the system or instrument of the present invention and/or each of its components or apparatuses or devices therein or thereof. The software product can comprise a certain number of software modules comprising at least one set of executable instruction(s) for enabling the computer means of the system to control and/or manage and/or operate the system and/or each of its components or apparatuses or devices therein or thereof.

The main features of this invention are given in the independent claims. Additional features of the present invention are given in the dependent claims.

The preparation of a liquid cell sample (in most cases whole blood) in an immunology or pathology laboratory is similar. The process of wash or non-wash of the whole blood offers two alternative procedures on how to perform the preparation method or procedure. In immunology labs the non-wash procedure is most often used, while in pathology labs the wash procedure is used in majority. In some cases a test sample must be centrifuged, in other cases not. Either way, the cell (pre)treating system or instrument according to the present invention can be used with great success, due to elaborate software for the computer means of the system, which opens up a flexibility of use.

The fact that the cell treating system or instrument, also called "FlowStainer" or "Flow Stainer", is a 4-in-1 system (1. cocktail mixer means, 2. carousel/centrifuge means, 3. lysing/washing assistant means, 4. means for pipetting of reagents and cell samples into daughter tubes) will make a normal size laboratory save between 1.000-3.000 work hours annually by using the present cell treating system.

The work routines of a lab engineer or lab assistant will also change dramatically using the FlowStainer by the fact that they can place a regular blood sample in the cell treating system and collect the test sample for direct placement in the Flow Cytometer without visiting the system once during its run time. Assistants working with pipetting of antibodies and other reagents will also find that work related health problems (such as e.g. shoulder and/or arm aches or pains) will dramatically decrease.

The features and advantages of the invention and the manner of realizing them will become more apparent, and the invention itself will best be understood, from the following detailed description and appended claims, with reference to the attached drawings showing some preferred embodiments of the invention.

BRIEF DESCRIPTION OF THE DRAWINGS

These and other aspects of the invention are apparent from and will be further elucidated, by way of example(s), with reference to the drawings, wherein.

DESCRIPTION OF THE PREFERRED EMBODIMENTS

Figure 1:
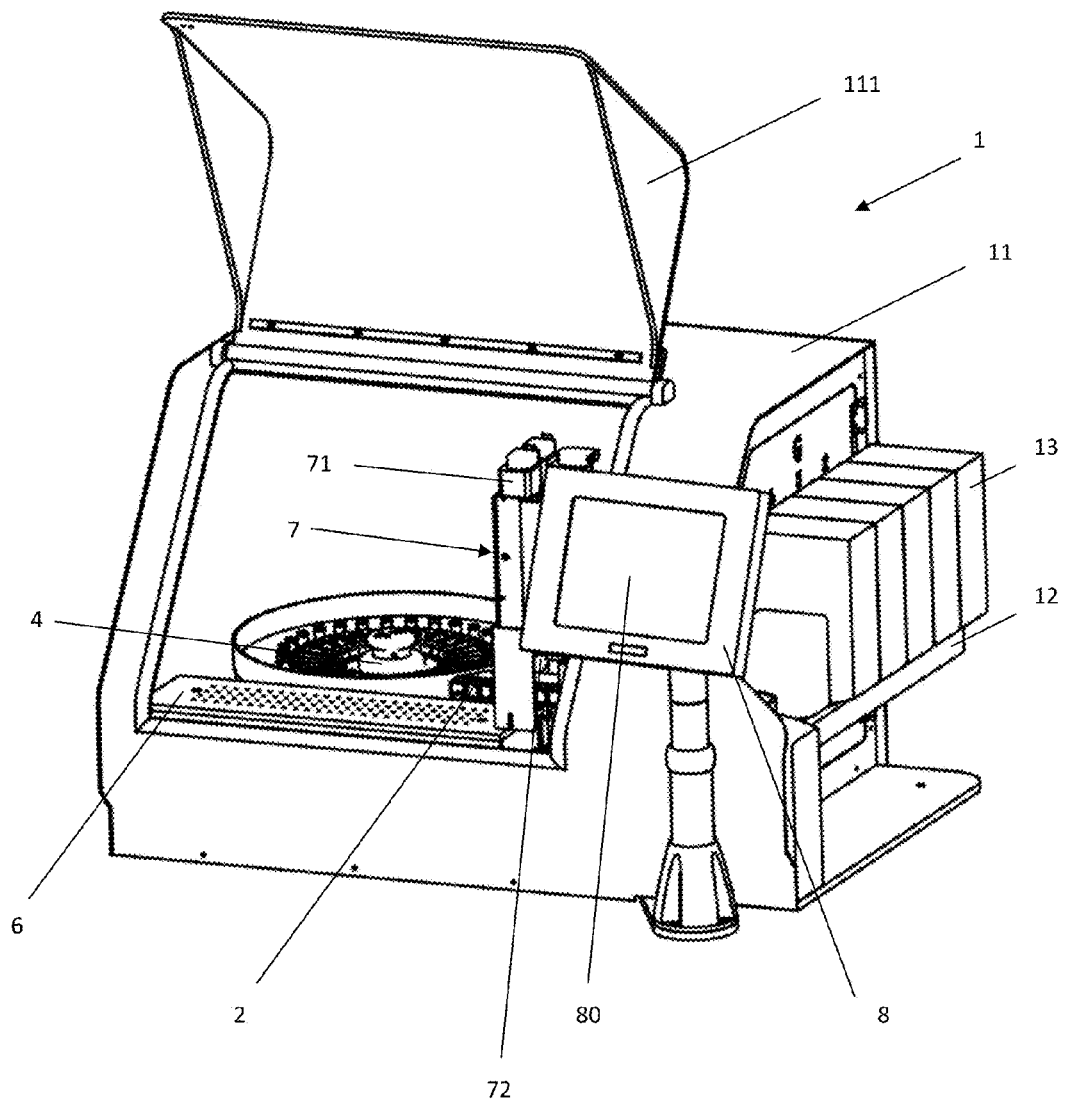
FIG. 1 is a perspective view of the cell treating system embodying the principles of the present invention.
Figure 2:
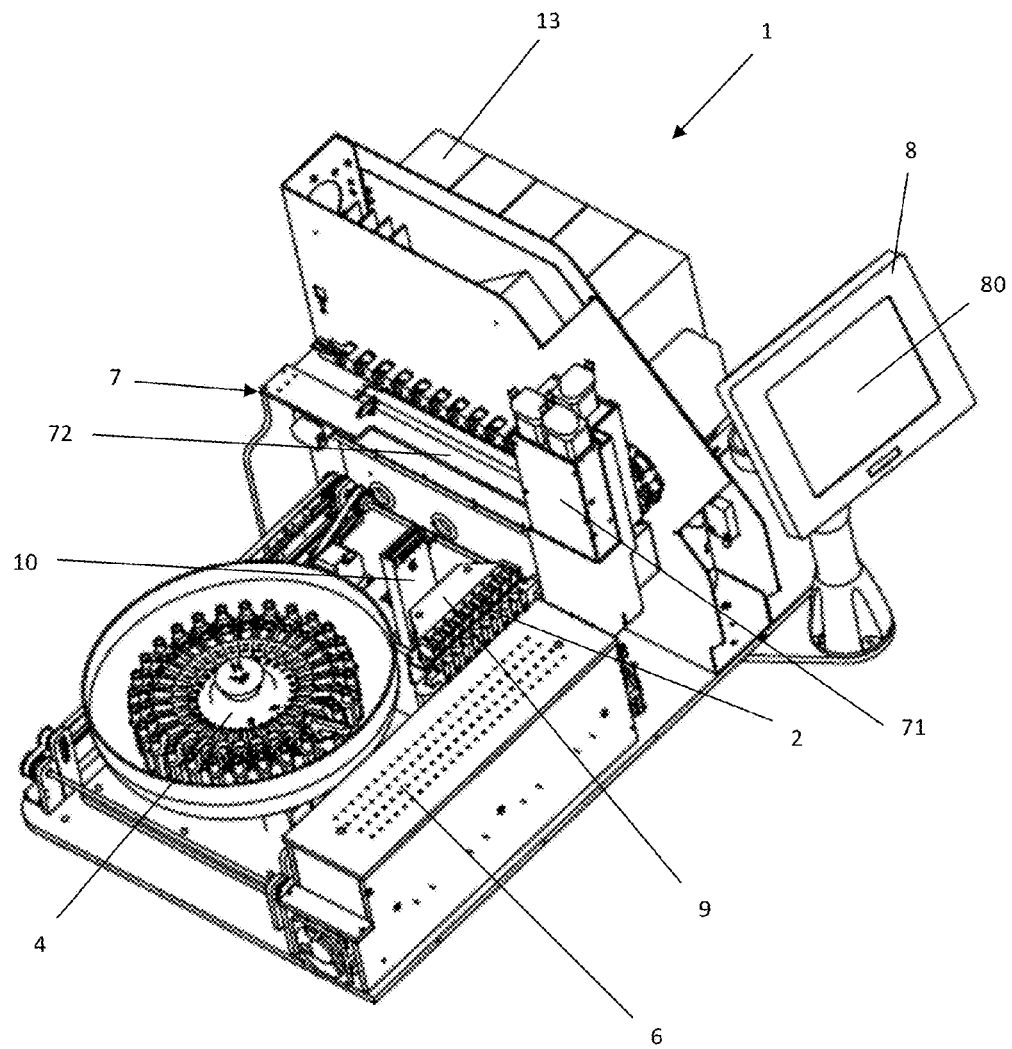
FIG. 2 is another perspective view of the system shown in FIG. 1 without some elements or parts of the system housing.

One embodiment of a compact cell treating system according to the present invention is generally designated by reference numeral 1 in FIGS. 1 and 2. The system 1 comprises a main test sample rack arrangement or means 2, a carousel/centrifuge arrangement or means 4, an antibody/stabilizer container and cooler arrangement or means 6, a robot arrangement or means 7, and a computer means 8. The system further comprises a reagent rack arrangement or means 12, wherein the reagent rack arrangement or means 12 is arranged to accommodate one or more reagent bottles 13, e.g. according to one with their necks and/or open-tops upside down. The system can also comprise a housing or case 11 having a lid or door or cover 111 moveably (providing for pivoting or sliding thereof) fastened to the housing 11 by a suitable hinging or fastening means.

The fully automated instrument or system 1 according to the present invention comprises specially designed and developed components/units/devices, such as e.g. the main test sample rack arrangement 2, the carousel/centrifuge arrangement 4, the antibody/stabilizer container and cooler arrangement 6, the robot arrangement 7, the computer means 8, different stations, etc. The full automatization of the pretreating cell sample process(es) is achieved with the help of the improved components/units/devices within the instrument that are cooperating and working together. For example, the robot arrangement 7 with the help of its arm and syringe arrangement provides for taking different cell samples from the main test sample rack arrangement 2 and putting them in the carousel/centrifuge arrangement 4 for treatment as well as for taking e.g. different stabilizers and/or antibodies from the antibody/stabilizer container and cooler arrangement 6 for adding to the different cell samples in the carousel/centrifuge arrangement 4. The multifunctional carousel/centrifuge arrangement 4 allows simultaneous pretreatment of several different cell samples and has several functionalities. The antibody/stabilizer container and cooler arrangement 6 not only holds the different stabilizers and/or antibodies and/or reagents and/or cocktails, but also provides for a desired environment (e.g. temperatures) in order to provide for storing for a long time without getting them ruined or changing some of their properties. All the processes and/or components/devices in the instrument or system 1 are controlled and operated by the computer means 8 having the appropriated for that software. Due to all that, the fully automated instrument or system 1 will provide for keeping all time limits connected with the preparation of the different cell samples, for reduced manpower working hours and for increased quality of the prepared cell samples, thus better results. Furthermore, as previously mentioned, the instrument 1 will provide for much time and labor saving compared to the time and labor consuming manual or partial/semi-automated cell pretreatment processes. The system or instrument 1 will also provide for cost optimization and/or logging of the use of expensive antibodies and/or reagents in the different cell preparation processes. The system or instrument 1 provides for standardization and/or reproducibility of desired procedures that are to be repeated in different and independent cell preparation operations or runs or procedures or protocols of the instrument. Finally, system or instrument 1 provides for minimizing or removing errors and non-uniformity of operation(s).

The reagent rack arrangement or means 12 can be adapted for big or great volumes of liquid(s), wherein the liquid(s) or fluid(s) can be at least one of the following: PBS (Phosphate Buffered Saline) liquid, lyse or lysing solution or liquid, physical saline water or solution, distilled water, rinsing or cleansing liquid(s) or fluid(s) or agent(s), etc.

Figure 3:
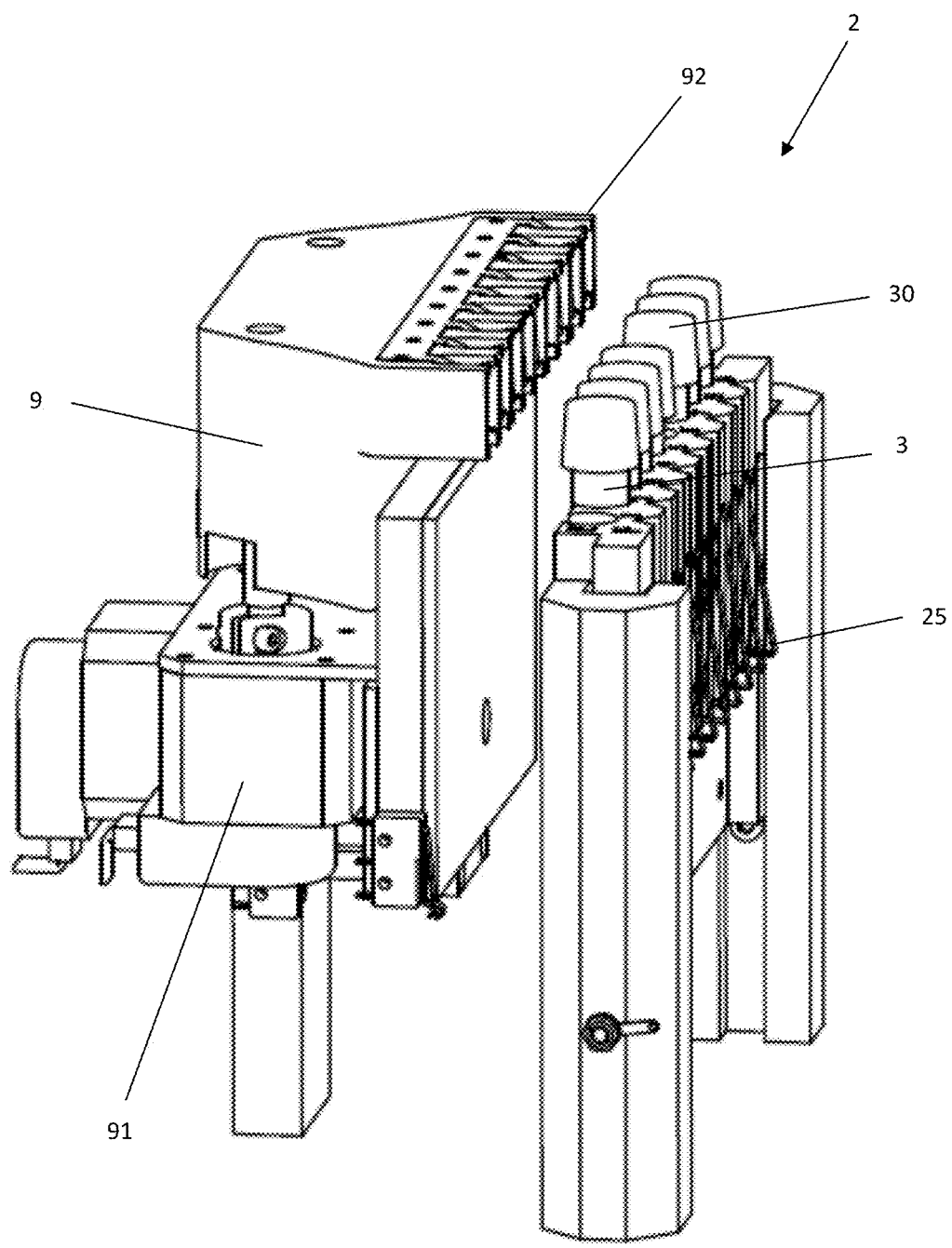
FIG. 3 shows one embodiment of a main test sample rack arrangement or means with a cap removing means.

The main test sample rack arrangement or means 2, shown in FIG. 3, can be detachable and is arranged for holding one or more sample containers 3, wherein the sample container has an open-top and can preferably be a test tube having its open-top locked or covered by a cap or cork or cover 30. The main test sample rack arrangement or means 2 further comprises, in its proximity, means 9 for automated removing of one or more sample container caps 30. The cap removing means 9 can further comprise a cap grabbing or holding means 92 for grabbing and/or holding at least one sample container cap or cover 30. The cap removing means 9 and/or its components (such as e.g. the cap grabbing or holding means 92) is operated and/or driven by at least one motor device 91 comprising suitable gearing and/or reduction means (not shown). The main test sample rack arrangement or means 2 can further comprise an additional sample container holding means 25 for holding one or more sample containers of a different type, such as e.g. small test tubes. The cap removing means 9 can further be adapted to put or set back the caps or corks or covers 30 onto the sample containers 3, e.g. after test sampling or sucking up blood sample.

Figure 4A:
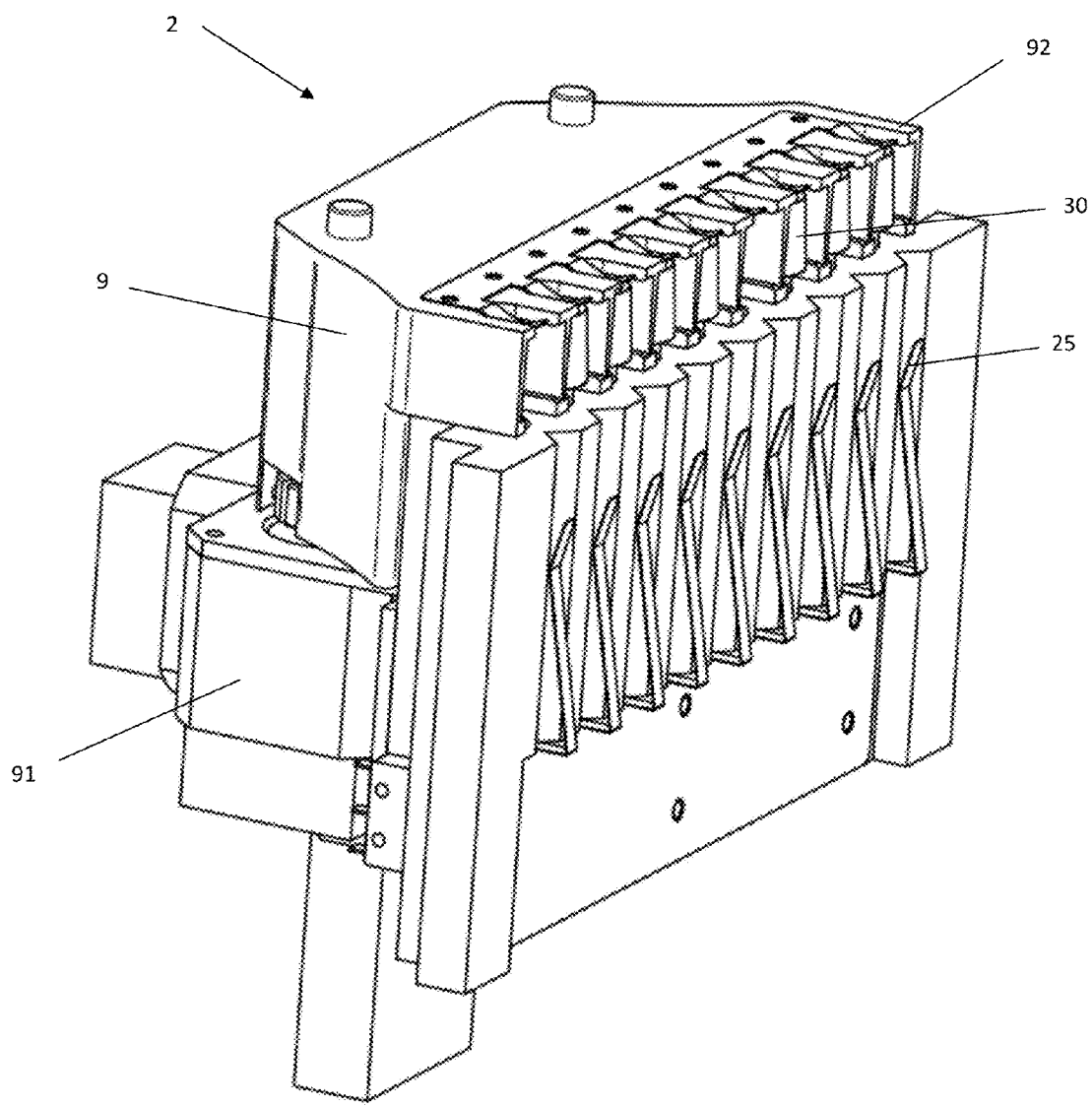
FIG. 4A shows the main test sample rack arrangement or means of FIG. 3 with the cap removing means holding the caps in order to penetrate a certain cap by a needle of a needle or syringe arrangement.

FIG. 4A shows the embodiment of the main test sample rack arrangement or means 2 from FIG. 3, wherein the caps or covers 30 are being held by the cap removing means 9, 91, 92, so that a needle of at least one needle or syringe arrangement or means would be able to penetrate a certain cap 30 in order to suck up blood from the mother sample tube or container 3, and then the needle will be able to retract without removing or separating the cap 30 from the certain test tube or container 3 and getting it stuck on said needle. With other words, the so-called holding or cap removing means 9, 91, 92 is thus able to hold the cap 30 during the whole above-mentioned process in order not to get it separated from the certain test tube or container 3.

Figure 4B:
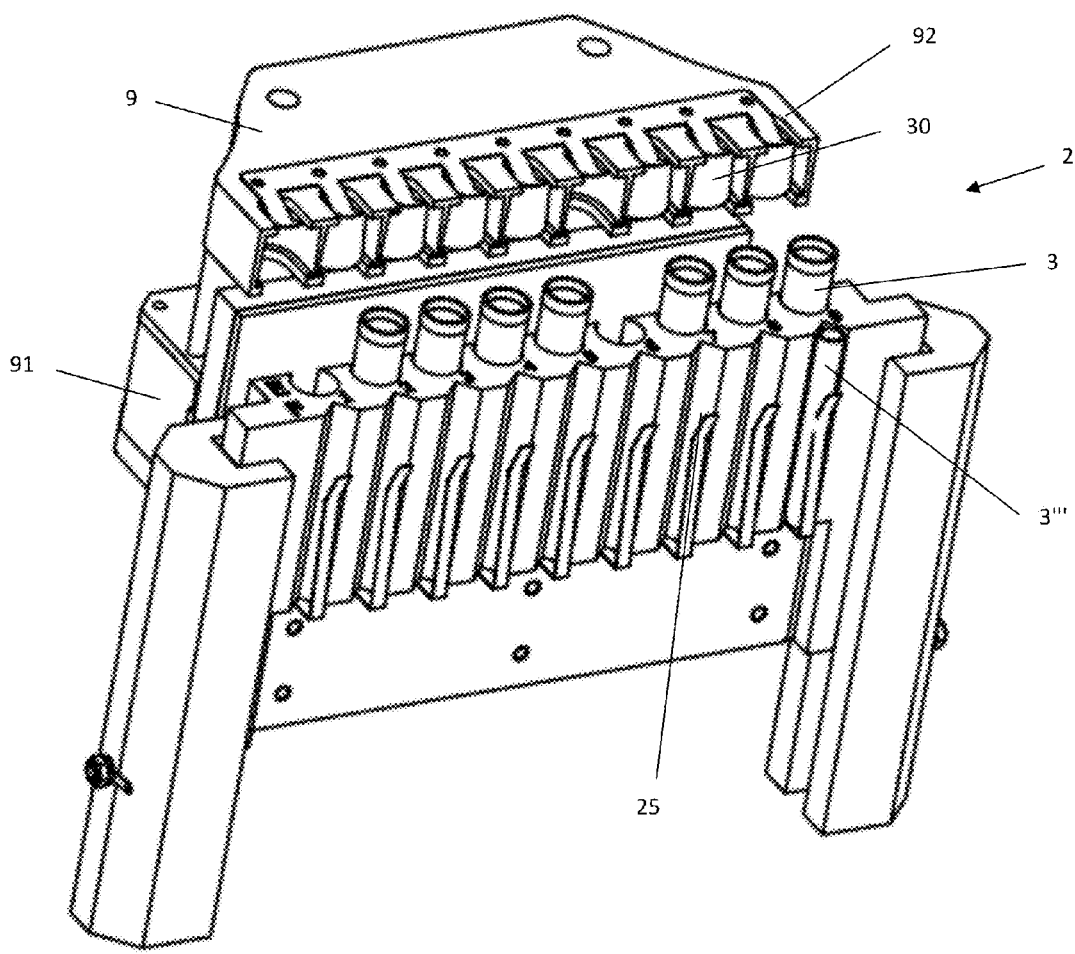
FIG. 4B shows the main test sample rack arrangement or means of FIG. 3 with the cap removing means, wherein the caps are removed.

FIG. 4B shows the embodiment of the main test sample rack arrangement or means 2 from FIG. 3, wherein the caps or covers 30 are removed from the sample containers 3 by the cap removing means 9, 91, 92. One different type sample container 3''', that is being held in said additional sample container holding means 25, is also shown in FIG. 4B.

Figure 9A:
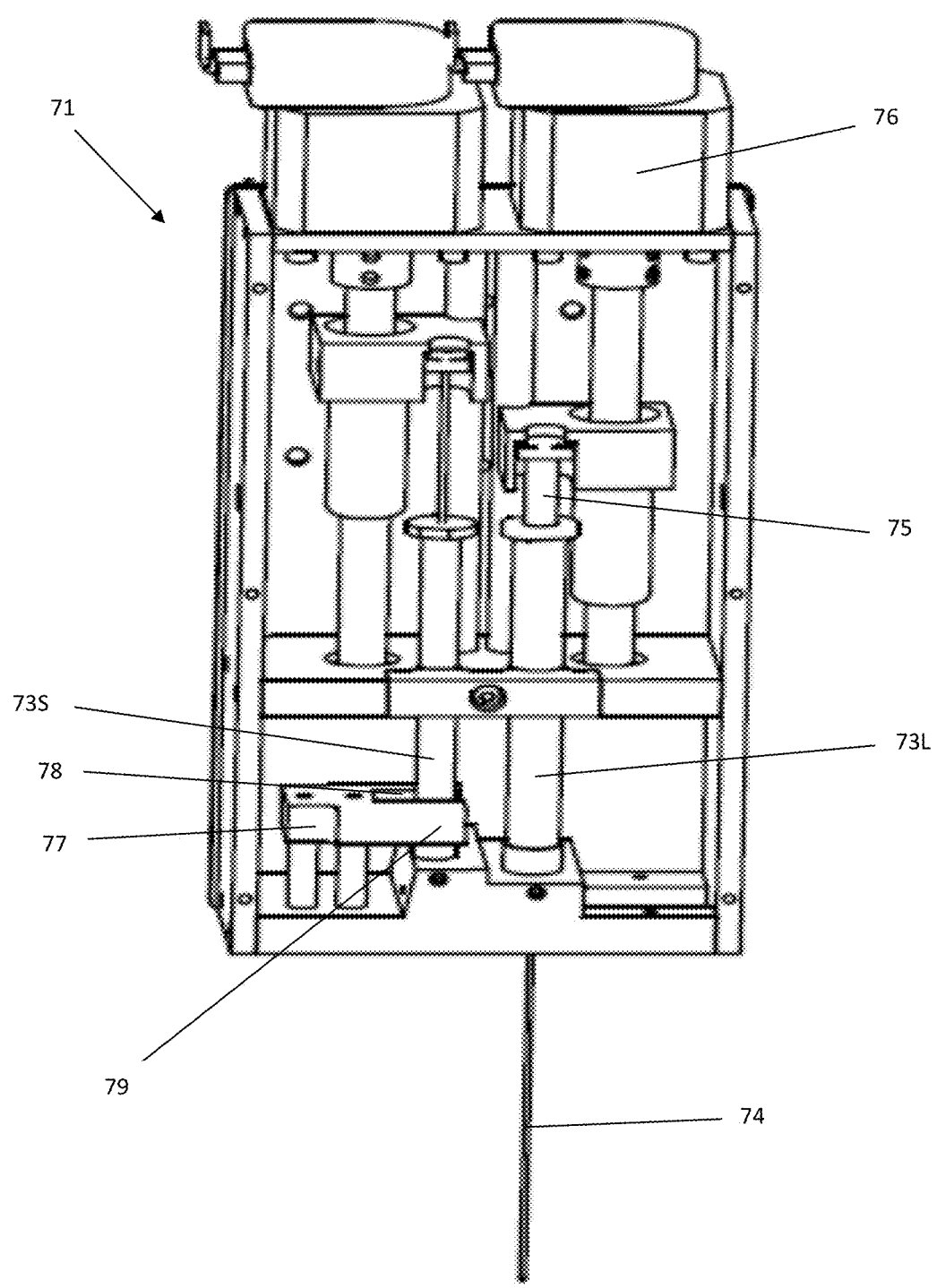
FIG. 9A-9B show different embodiments of a needle or syringe arrangement or means the according to the present invention.
Figure 9B:
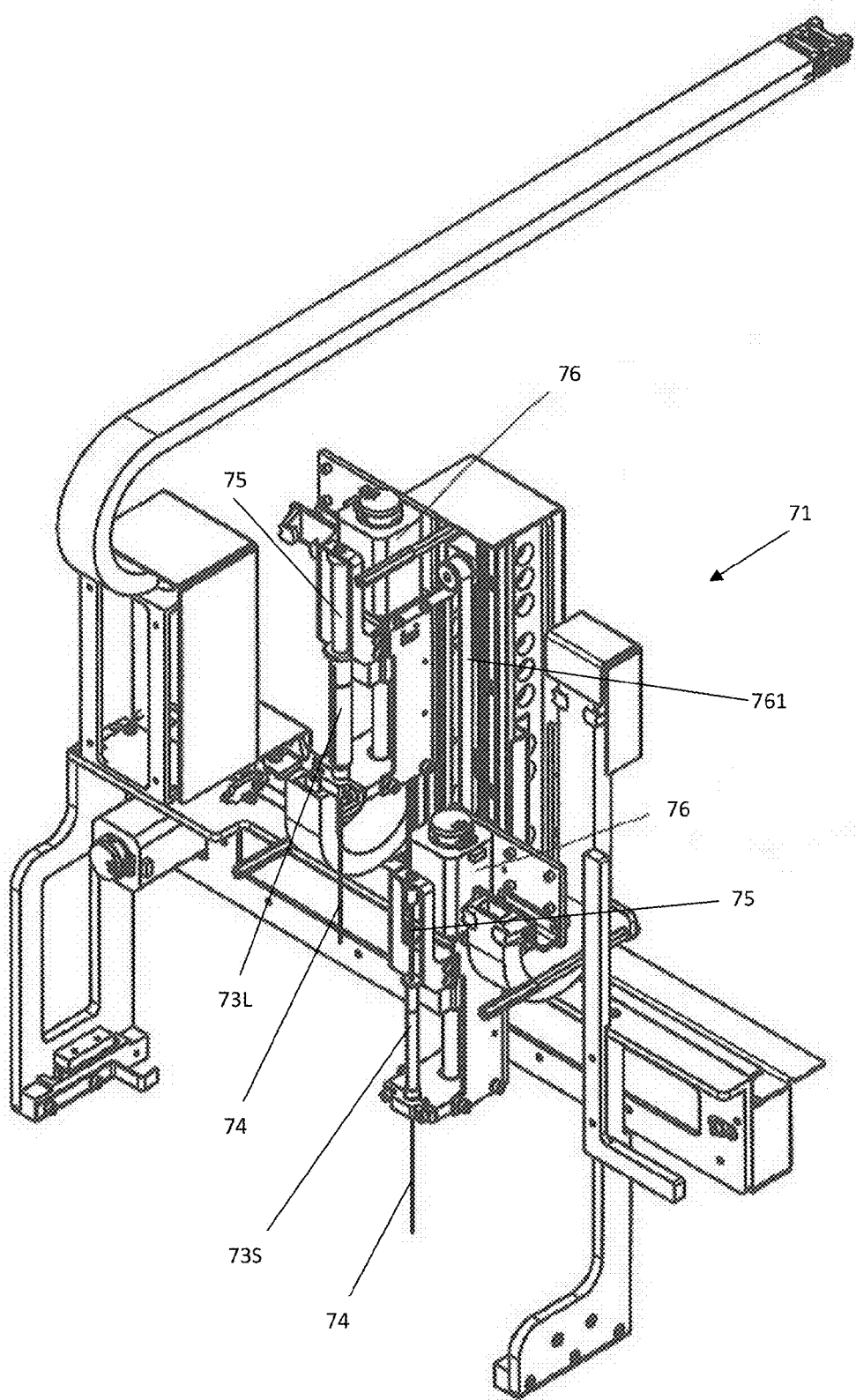

As shown in FIGS. 1, 2 and 9, the robot arrangement or means 7 is adapted or arranged for mechanically or physically serving the system or instrument 1 and comprises at least one arm arrangement 72 and at least one needle or syringe arrangement or means 71 that can be mounted on said at least one arm arrangement 72 and can comprise at least one of: syringe, needle, plunger. In one embodiment the needle or syringe arrangement or means 71 can comprise: i) two syringes 73S, 73L placed substantially vertically and parallel with each other and operated by at least one motor driven mechanism 76, wherein one syringe 73S is adapted for small volumes of liquid(s) (within e.g. the microliter (µl) range) and the other syringe 73L is adapted for big or large volumes of liquid(s) (within e.g. the milliliter (ml) range): and ii) one common needle 74 arranged and adapted for servicing and working with both syringes 73S, 73L (FIG. 9A). Alternatively, there can be arranged a separate needle for each syringe in the arrangement (FIG. 9B). In another embodiment each syringe 73S, 73L can be operated independently by its own motor driven mechanism 76. The robot arrangement or means 7 can comprise three axes (x,y,z) and together with its elements/components allows and provides for movement of said at least one needle or syringe arrangement or means 71 in all directions within the x,y,z or 3D (three dimensional) area or space of the system 1. The plunger 75 of the syringe in the syringe arrangement or means 71 can be operated, e.g. pushed up or down, by said at least one motor driven mechanism 76.

The system 1 can further comprise a rinsing or rinse arrangement or station 10, shown in FIG. 2, wherein said at least one needle of said at least one needle or syringe arrangement or means 71 can be cleansed or rinsed with the help of at least one cleansing or rinsing fluid or liquid or solution and/or chemical, such as e.g. distilled water, but not limited only thereto. The cleansing or rinsing arrangement 10 can comprise at least one or a predetermined number of chambers and/or bottles having automated supply of said at least one cleansing or rinsing fluid or liquid or solution and/or chemical for internal and external cleansing of the syringes and/or needle(s)/cannula(s). The cleansing or rinsing arrangement 10 can further comprise at least one wasting chamber or bottle or container, wherein the test sample syringes can pump out the used cleansing or rinsing fluid(s) and/or chemical(s). The cleansing or rinsing arrangement 10 can further comprise pumping means 90 for pumping waste fluid(s) into at least one waste bottle or chamber or container 95 (of a waste station 95), shown in FIG. 10. At least one bottle 13 with rinsing liquid or chemical from the reagent rack arrangement or means 12 can be connected to the cleansing or rinsing arrangement or station 10. In addition the waste station comprising said at least one waste bottle or chamber or container 95 can further comprise sensor means for detecting liquid level in said at least one waste bottle or chamber 95 and for sending the liquid level data to the computer means 8 so that when said at least one waste bottle or chamber 95 is full with liquid the computer means 8 will produce and send to the lab assistant or operator a message asking and/or requiring emptying of the full waste bottle or chamber 95 or replacing it with an empty one.

The computer means 8 comprises at least one CPU (not shown) and is provided for control and/or operation and/or management of all components, apparatuses or devices in the system 1. The computer means 8 can further comprise a screen or display 80 (output interface) and/or a keyboard or a keyset of button(s) (input interface). In one embodiment said screen or display 80 is a touch screen, wherein a keyboard or at least one button can be visualized on the touch screen.

A suitable software product that can comprise a certain number of software modules and be stored on a readable or recordable media (not shown) and can further comprise at least one set of instruction(s) to enable the computer means 8 to provide for control and/or management and/or operation of the system 1 and/or each of its components or apparatuses or devices therein or thereof, e.g. by executing at least one instruction.

The computer means 8 can comprise memory means (not shown) for storing different kinds of software modules, various information and/or data, etc., such as e.g. current positions, volume amounts and expiration dates for antibodies/stabilizers/reagents in e.g. the antibody and cooler arrangement 6 and/or the reagent rack arrangement 12.

The system or instrument 1 can have means (not shown) for wired and/or wireless and/or Bluetooth® communication with external devices, such as, but not limited to, a printer (e.g., for printing a protocol list or an antibody/reagent list, etc.), or an external PC or tablet or notebook or cell phone. It can also be possible to send a message to the external PC or tablet/notebook or cell phone, or the like, in order to inform the lab assistant or engineer that a certain test sample preparation has been completed, give him/her some other warning or result messages, etc.

Figure 5A:
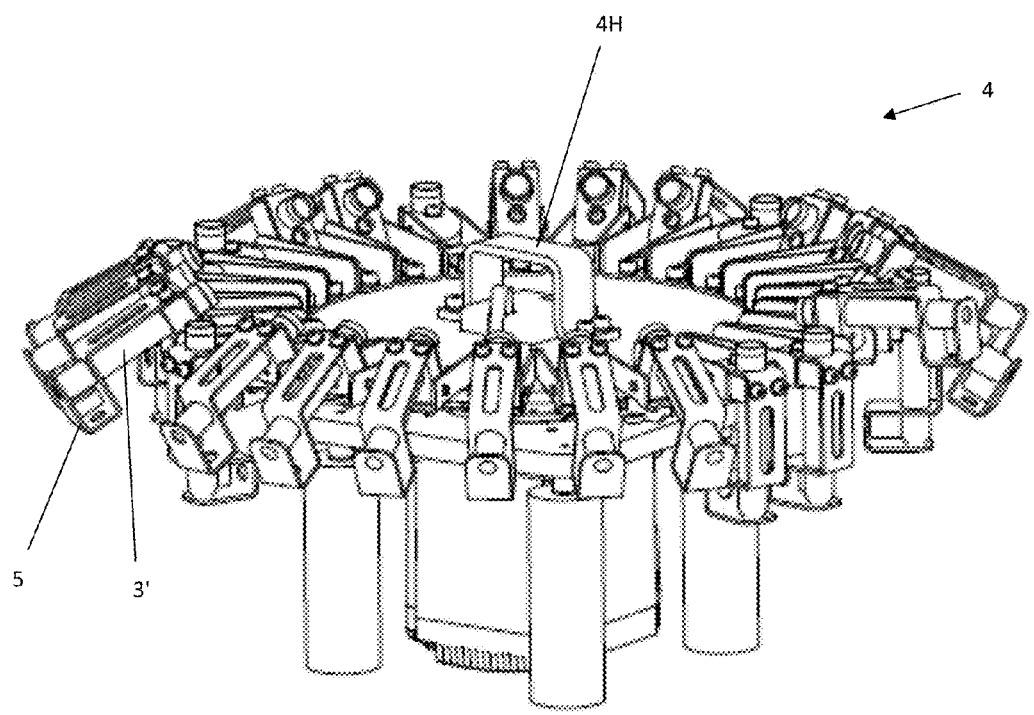
FIG. 5A-5D show different embodiments of a carousel/centrifuge arrangement or means comprising a number of sample container holders.
Figure 5B:
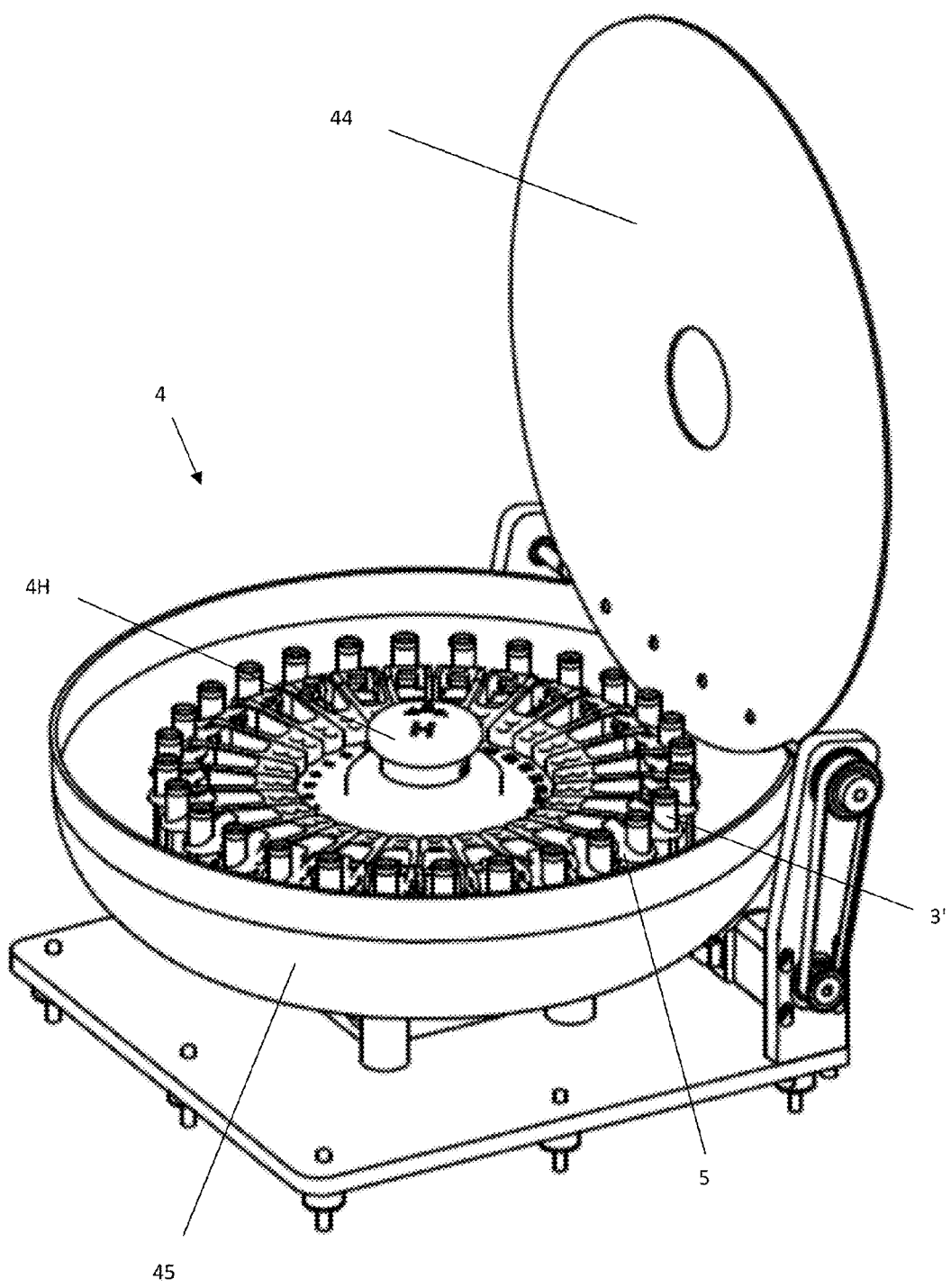

The two embodiments of the carousel/centrifuge arrangement or means 4, shown in FIG. 5A-5B, comprise a certain number of holder means 5 for secondary or daughter test or sample containers 3'. Said two embodiments disclose two different alternatives of the test tube holder means 5. Within the holder housing 50, shown in FIG. 6A-7D, of each holder means 5 having titrating and/or shaking functions, there can be arranged an optical fiber detection means (not shown) for detecting whether a secondary or daughter test or sample container 3' has been placed in the holder means 5 when in its rest or down or lowest position. Additionally, the carousel/centrifuge arrangement or means 4 can further comprise a housing 45 and a mechanically or motor driven or operated lid or lock 44.

FIGS. 6A-6B and 7A-7D show the two embodiments of the carousel/centrifuge arrangement or means 4 according to the present invention, which illustrate and give several details than what is shown in FIG. 5A-5B.

The carousel/centrifuge arrangement or means 4 further comprises a motor drive arrangement or means 41 allowing for movement or centrifuging in clockwise and/or counter-clockwise direction. The carousel/centrifuge arrangement or means 4 can function as a centrifuge and further apply the "swinging bucket" principle (that can allow the cells to get gathered on the bottom of the daughter sample containers or test tubes 3'). In some cases it can be estimated that the cell volume in a sample can be small and/or that the cells can be weakened and could not manage to take or bear a hard spin (i.e. centrifuging at high speed(s) providing for great or big G-forces). In order to ensure that sample cells would tolerate or endure the treatment and that enough cell population would be provided for the later analyzing in the flow cytometer, the lab engineer or assistant can in some cases select a more careful centrifugation. There is a hypothesis that larger or heavier cells and smaller or lighter cells will be sorted if the centrifuging speed is increased gradually. In the above cases, it is important that the centrifuge arrangement has default and/or desired centrifuging speed rate(s). In some cases, washing a blood or cell sample can, for example, be selected where centrifugation is included in this process. Therefore, it can be important and/or desired to use a carousel/centrifuge arrangement 4 designed and constructed with the possibilities to provide for different G-forces for different cases in one and same preparation procedure or protocol. As there can be different cell samples within the different daughter sample containers or test tubes 3' and/or different cell types within one cell sample in one daughter sample containers or test tubes 3', possibly requiring different pretreatments, the motor arrangement 41 of the carousel/centrifuge arrangement 4 can be adapted and/or arranged for centrifuging with different speeds, depending on the cell types of the samples.

Figure 6A:
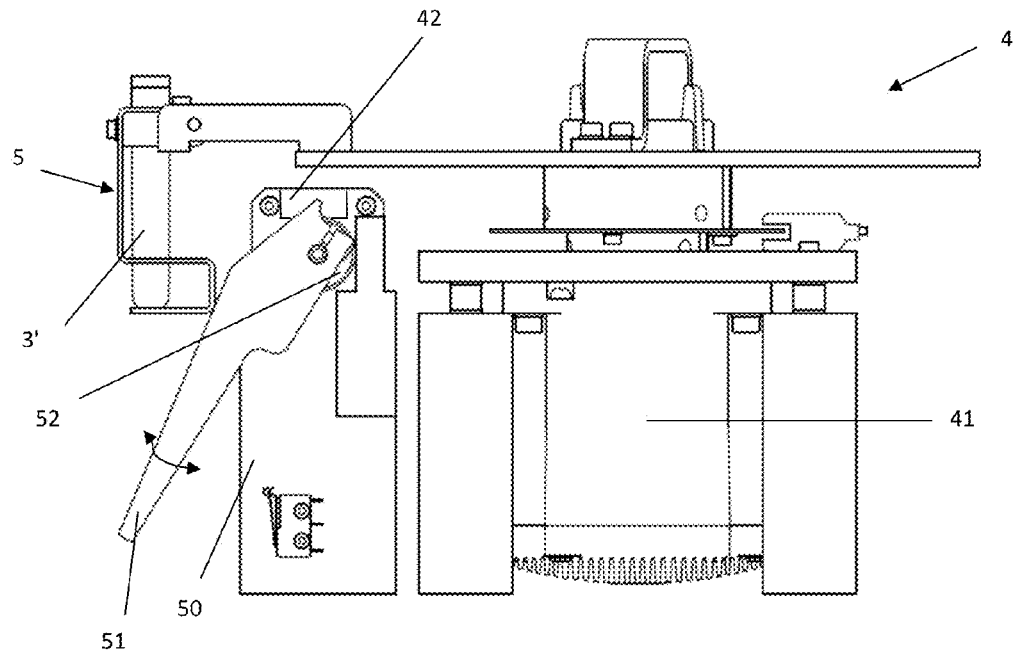
FIG. 6A-6B show two embodiments of one sample container holder arrangement of the carousel/centrifuge arrangement or means.
Figure 6B:
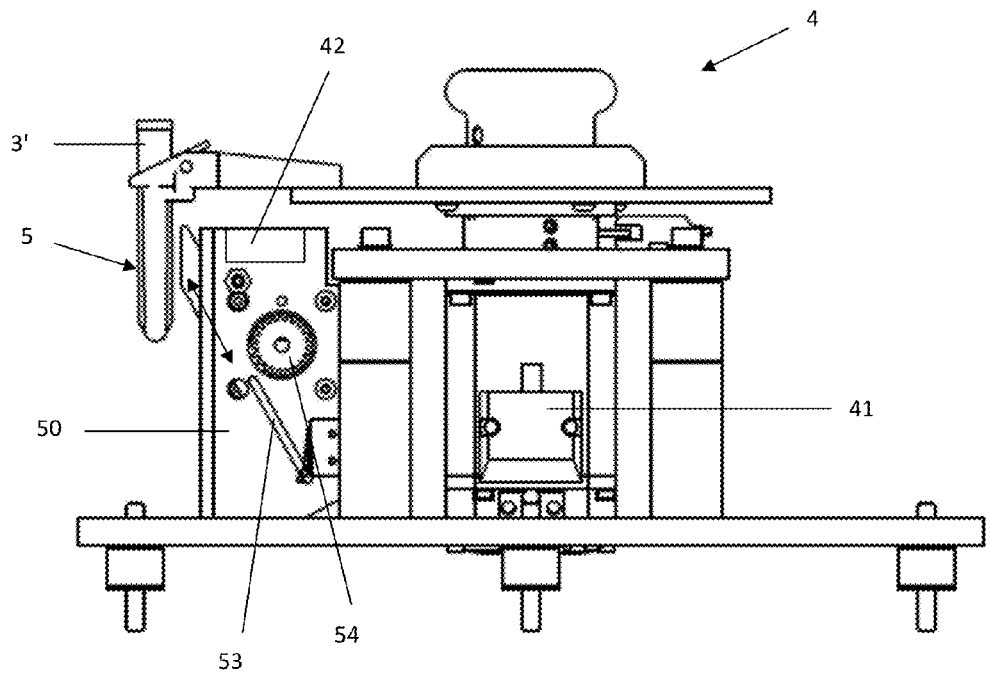
Figure 7A:
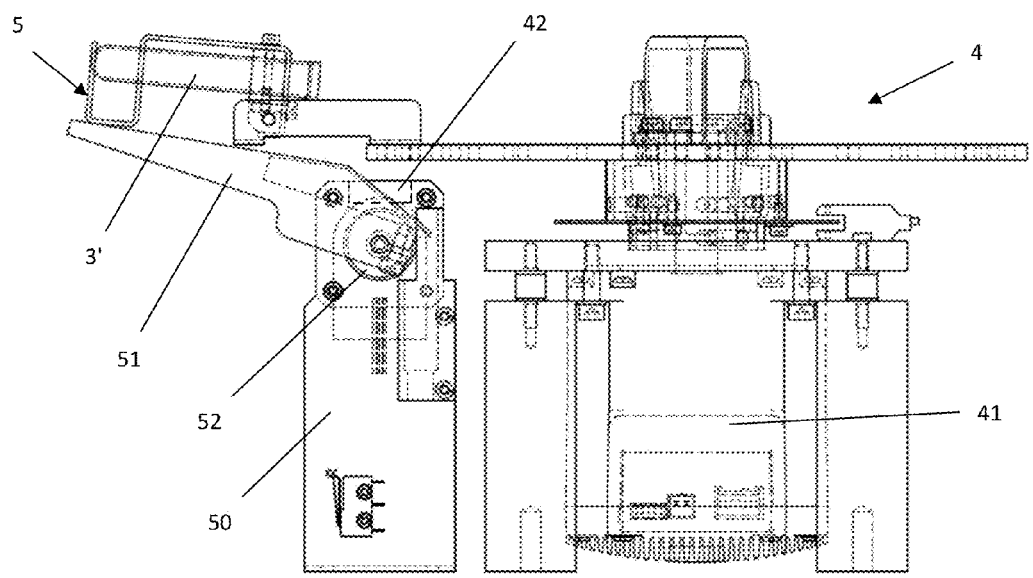
FIG. 7A-7D show two embodiments of said one sample container holder arrangement of the carousel/centrifuge arrangement or means (FIG. 7A-7B), and some elements (FIG. 7C-7D) thereof, in a different position from what is shown in FIG. 6A-6B.
Figure 7B:
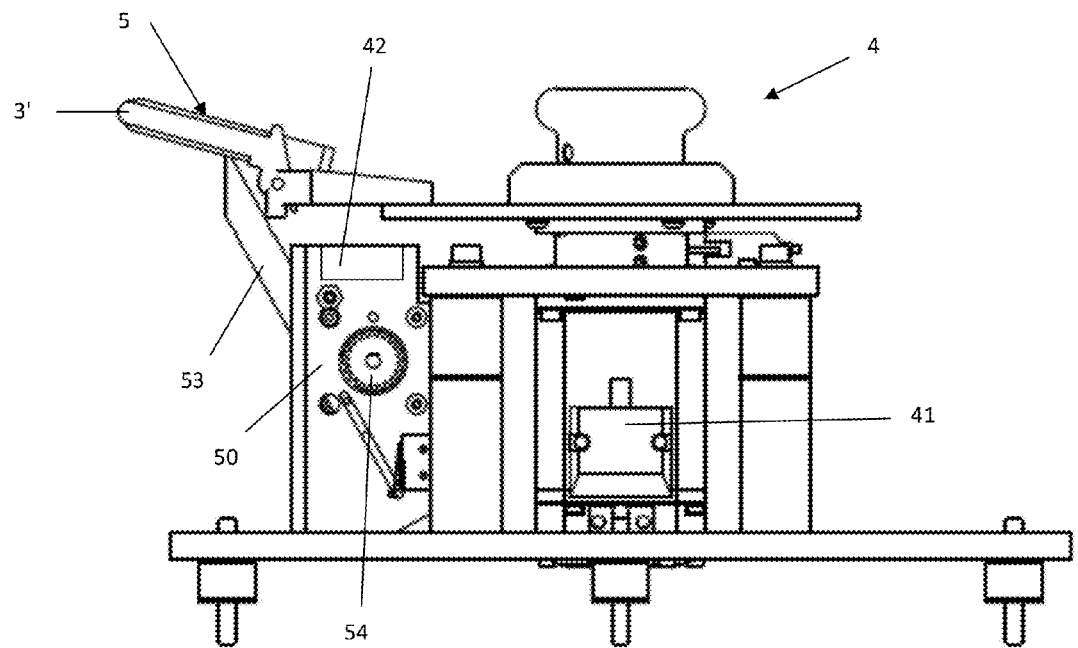
Figure 7C:
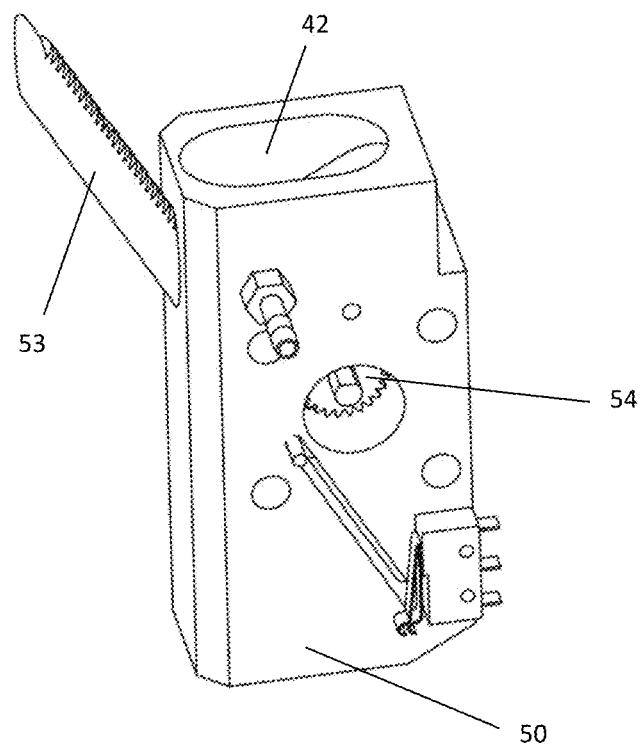
Figure 7D:
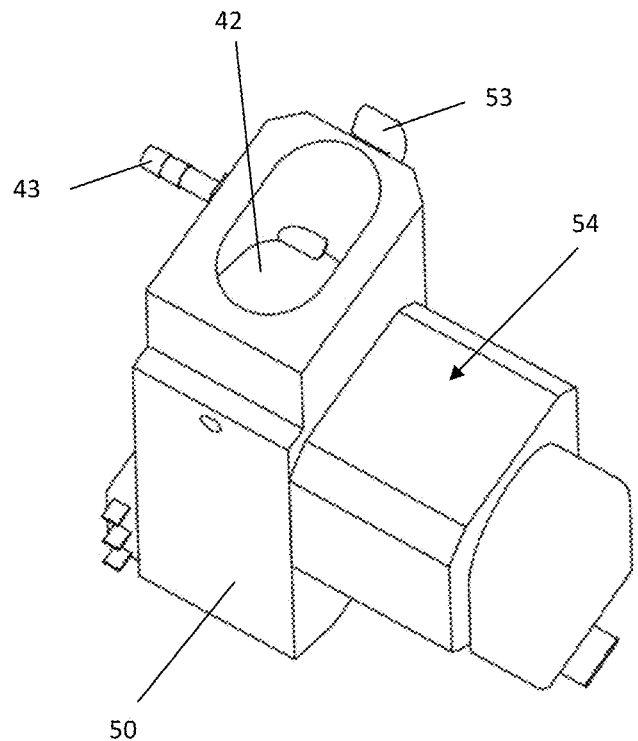
Figure 8A:
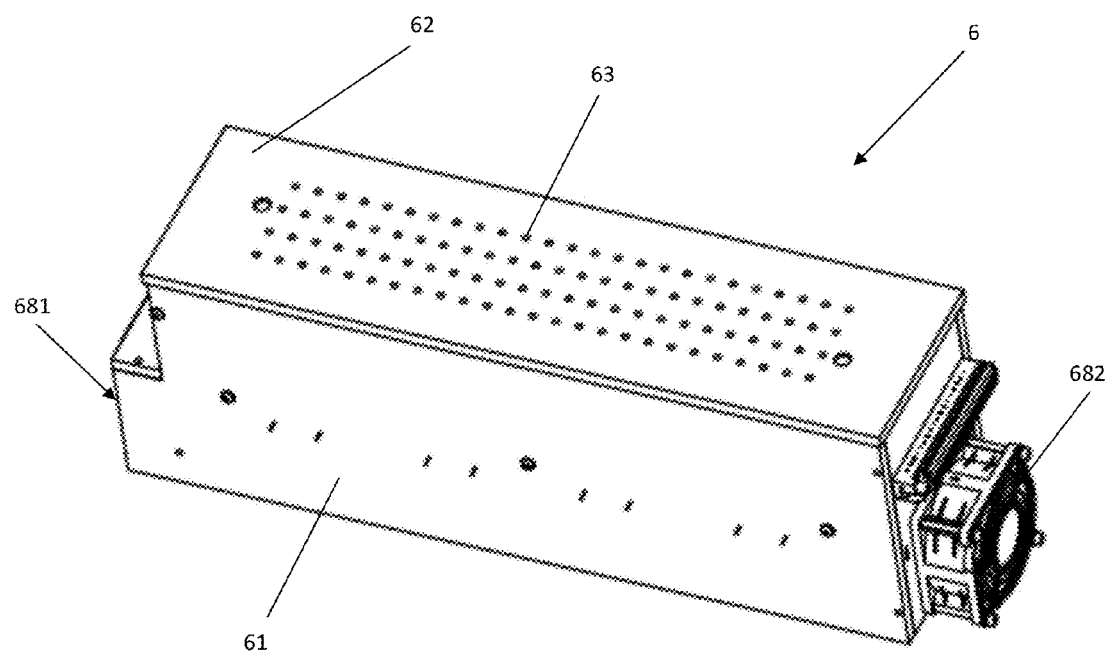
FIG. 8A-8D show different embodiments of an antibody/stabilizer container and cooler arrangement or means.
Figure 8B:
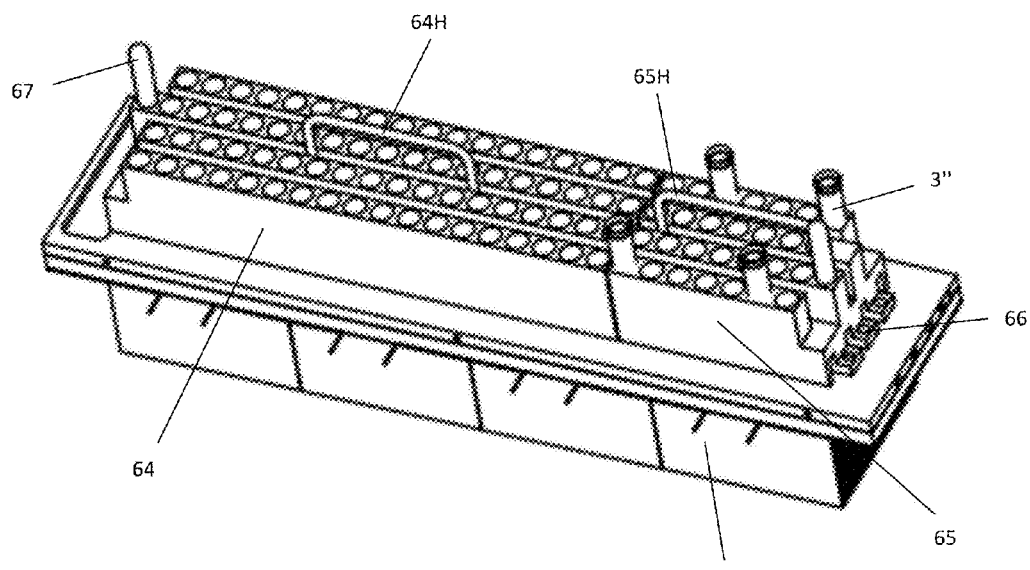
Figure 8C:
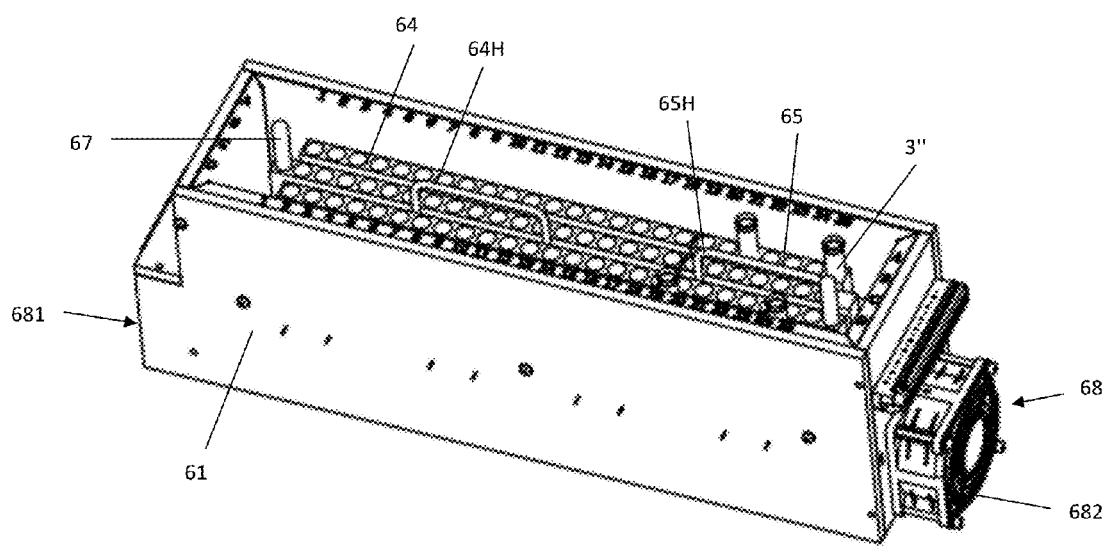
Figure 8D:
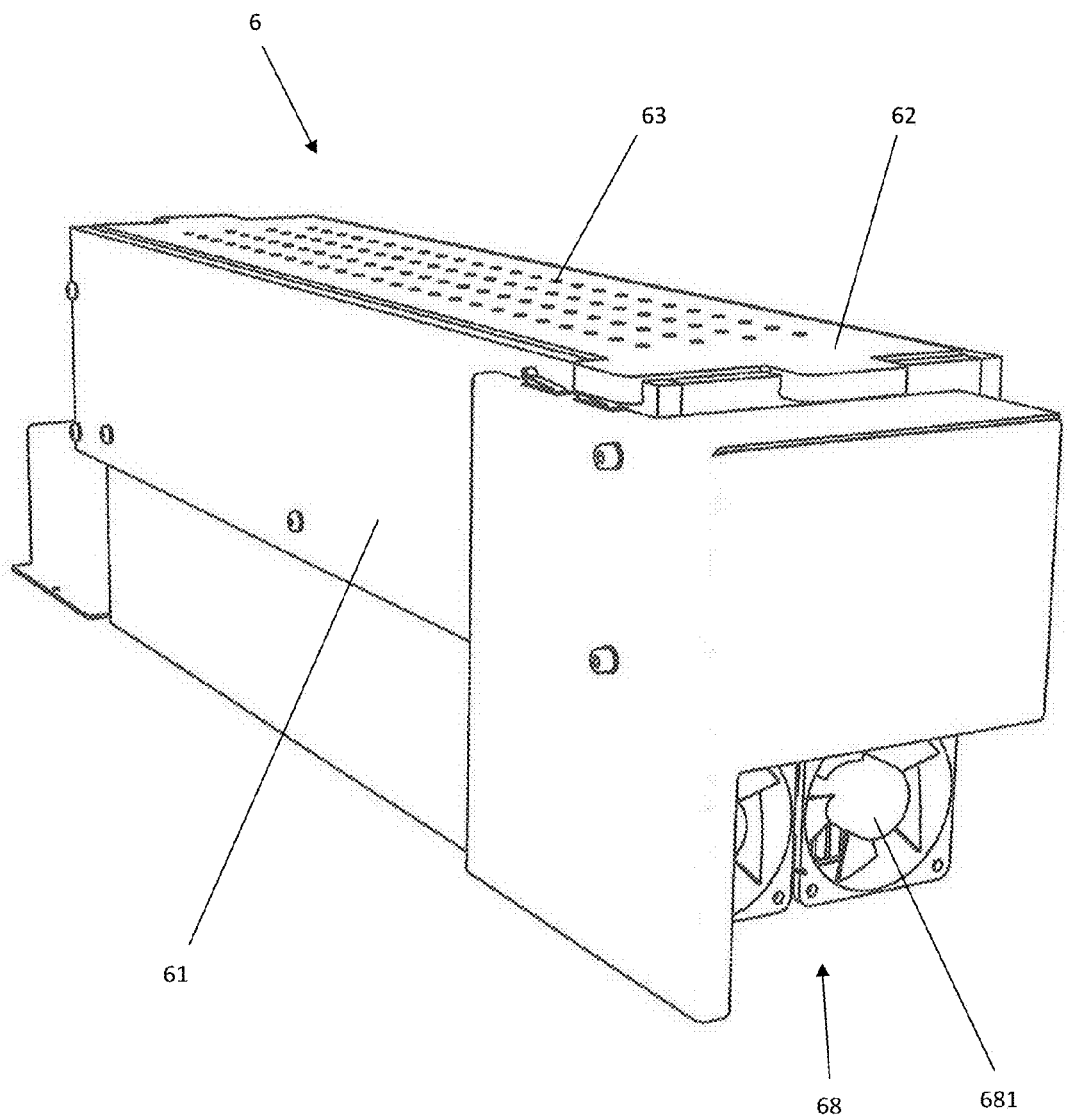

Centrifuging with different speeds can be necessary in order not to damage the different sample cells, to achieve better separation of the different sample cells, and to provide for each lab to choose a desired centrifuging speed (e.g., due to different requirements, regulations or practices in the different countries and/or labs). This will thus provide for achieving better results and can, for example, be provided by the motor arrangement 41 further comprising, but not limited only to, a servomotor. The centrifugation speed can be changed during one centrifugation step or period, and/or one centrifugation speed can be used under one centrifugation step or period and another different centrifugation speed can be used during another subsequent centrifugation step or period, and/or any possible combination thereof. For example, during one and same preparation procedure or protocol, under a first centrifugation period a first centrifugation speed can be used, under a second centrifugation period a second centrifugation speed can be used, and under a third centrifugation period at least two centrifugation speeds can be used and/or the centrifugation speed can be gradually increased, etc. Of course, the centrifugation periods and the centrifugation speeds can be combined and/or varied in any suitable way or manner for the pretreatment process(es). There can also be different time intervals providing for states of rest in between the different centrifugation periods. The motor drive arrangement 41 can be arranged to provide for G-forces over 200 g (and preferably under 1000 g, and most preferably under 600 g during the centrifugation(s). All movements and/or rotations and/or centrifugation speeds of the carousel/centrifuge arrangement or means 4 can be programmed and/or stored in the computer means 8. It can be important to be able to quickly pick up a desired application in order to use it again, without having to program it again. In order to detect any differences in the sample results in retrospect, it can in addition be important to be able to log all these data. For example the mixing and/or shaking of the test samples can be done by short and quick rotational movements in clockwise and/or anticlockwise direction. According to the first embodiment (FIG. 5A, 6A, 7A) the carousel/centrifuge arrangement or means 4 can further comprise titrating or shaking arm or means 51 that can be driven by a motor arrangement or device 52 in order to shake and/or vortex the contents of the test tube or sample container 3'. In FIG. 6A two opposite (up and down) movements of the titrating or shaking arm or means 51 are shown with arrows. According to the second embodiment (FIG. 5B, 6B, 7B-7D) the titrating or shaking function of the carousel/centrifuge arrangement or means 4 can alternatively be performed or executed by a pitch rack or pinion means 53 operated by a motor driven gear-wheel means 54. In FIG. 6B two opposite (up and down) movements of the titrating or shaking pitch rack or pinion means 53 are shown with arrows. In addition the titrating or shaking arm or means 51 of the first embodiment can be adapted to lift up, as shown in FIG. 7A, the test tube holder means 5 in order to empty or pour out exceeding liquid from the secondary or daughter test tube or sample container 3' into an exceeding liquid wasting means 42 (FIG. 7C-7D), which can be connected to the waste station 95. Alternatively, the titrating or shaking pitch rack or pinion means 53 of the second embodiment can be adapted to lift up, as shown in FIG. 7B-7C, the test tube holder means 5 in order to empty or pour out exceeding liquid from the secondary or daughter test tube or sample container 3' into an exceeding liquid wasting means 42 (FIG. 7C-7D), which can be connected to the waste station 95. As it is evident from FIG. 7A-7B, in order to pour out the unnecessary liquid, the daughter test tube or sample container 3' placed within the test tube holder means 5 can be rotated over 90° around the open top (side or end) of the daughter test tube or sample container 3' and wherein the substantially vertical position of the daughter test tube or sample container 3' is regarded to be positioned at approximately 0°. In other words, the arm 51 or the pinion 53 of the titrating and/or shaking arrangement 51; 53 provides for rotating and/or lifting up of the daughter test tube or sample container 3' placed within the test tube holder means 5, so that the bottom (side) of the daughter test tube or sample container 3' will get over or above the open top (side) of the daughter test tube or sample container 3', considered with respect to the horizontal line, thus providing for emptying or spilling or pouring out of the unnecessary liquid within or into the liquid wasting means 42 of the carousel/centrifuge arrangement 4. The titrating or shaking arm 51 and the titrating or shaking pitch rack or pinion means 53, respectively the motor arrangement or device 52 and motor driven gear-wheel means 54, of said two embodiments can be summarized and called for a titrating or shaking arrangement 51; 53, and a motor driven arrangement 52; 54, respectively. The exceeding liquid wasting means 42 can be a kind of a chamber or compartment or room/cavity within the holder housing 50 and above the motor driven arrangement 52; 54 and having an outlet 43 (FIG. 7D) for facilitating coupling or connecting with the help of suitable means to said waste station 95.

Furthermore, the carousel/centrifuge arrangement or means 4 can be made detachable. The carousel/centrifuge arrangement or means 4 can additionally comprise a handle 4H, shown in FIG. 5A-5B, in order to be easily taken out from the system 1. In order to secure the centrifuging process of the carousel/centrifuge arrangement or means 4 a sensor means, e.g. but not limited to reflecting laser sensor means, are used for confirming locked position of the carousel/centrifuge device and/or its handle 4H. The same or additional sensor means can be used to determine that the mechanically or motor driven or operated lid or lock 44 of the carousel/centrifuge arrangement or means 4 is in its closed or locked position. Should the operator attempt to open the carousel/centrifuge lid or lock 44 during the centrifuging process, an alarm means will warn the operator at the same time as the carousel/centrifuge device is being quickly stopped and controlled, and the operator will have no possibility to reach any moving parts.

Below there are described two possible embodiments providing incubation and/or lysing in the dark. Incubation and/or lysing should preferably be done in the dark, because light can have negative effect(s) on the sample(s). UV rays can also affect the reaction(s) negatively. Moreover, time and temperature can in addition affect the incubation and/or lysing process(es). Incubation (in the dark) is usually used to create a reaction between the cells and the reagent(s) and/or antibodies supplied to the cell sample.

Furthermore, in an alternative embodiment of the present invention, the lid 44 and housing 45 of the carousel/centrifuge arrangement or means 4 can be made of light reductive and/or non-transparent material, so that when the lid 44 is in a closed position with respect to the housing 45, both the lid 44 and the housing 45 will be arranged to thus provide for incubation and/or lysing (of the processed or (pre)treated cell samples) in the dark and/or excluding damaging UV-rays within the carousel/centrifuge arrangement 4 (of the instrument 1). This means that light will not be allowed within the carousel/centrifuge arrangement 4 when the lid 44 is in a closed position with respect to the housing 45.

Figure 5C:
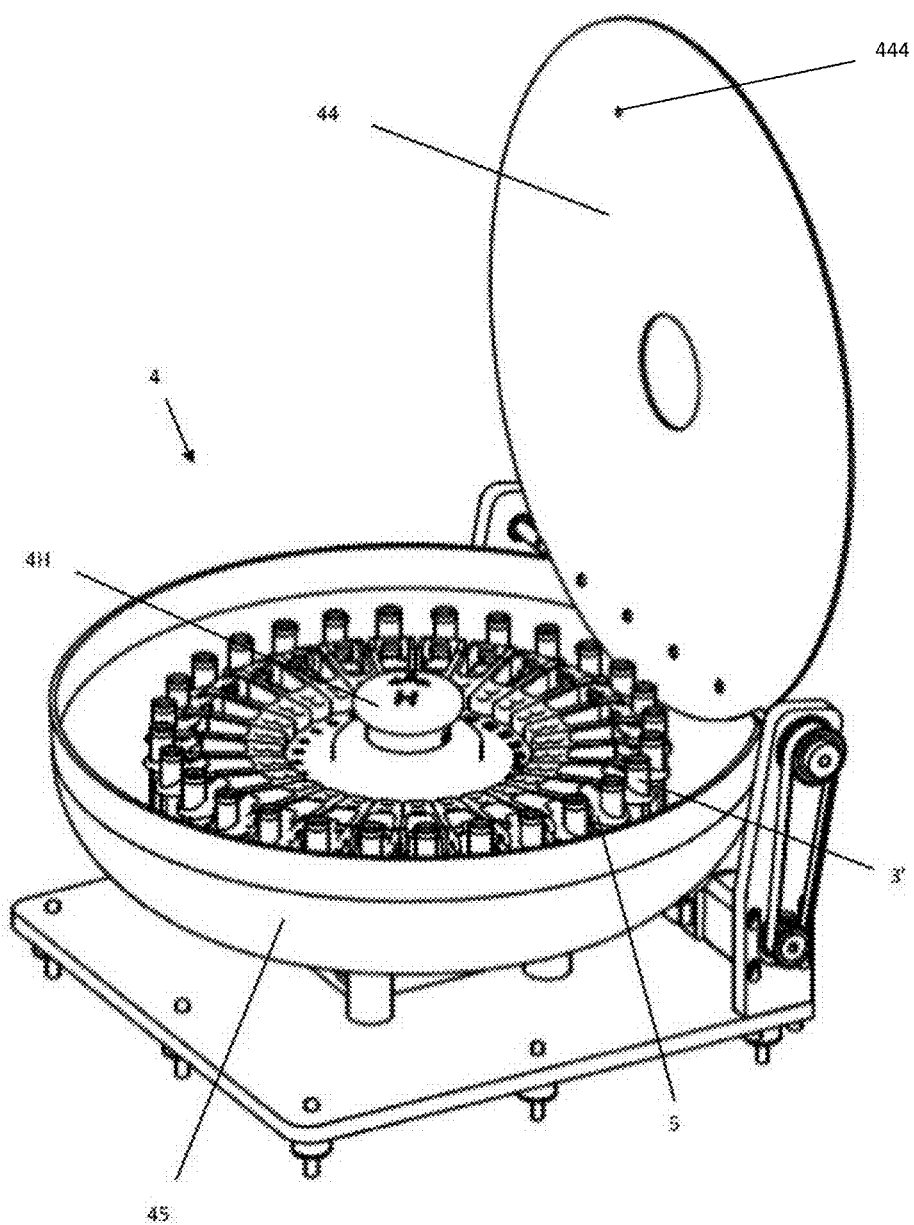
Figure 5D:
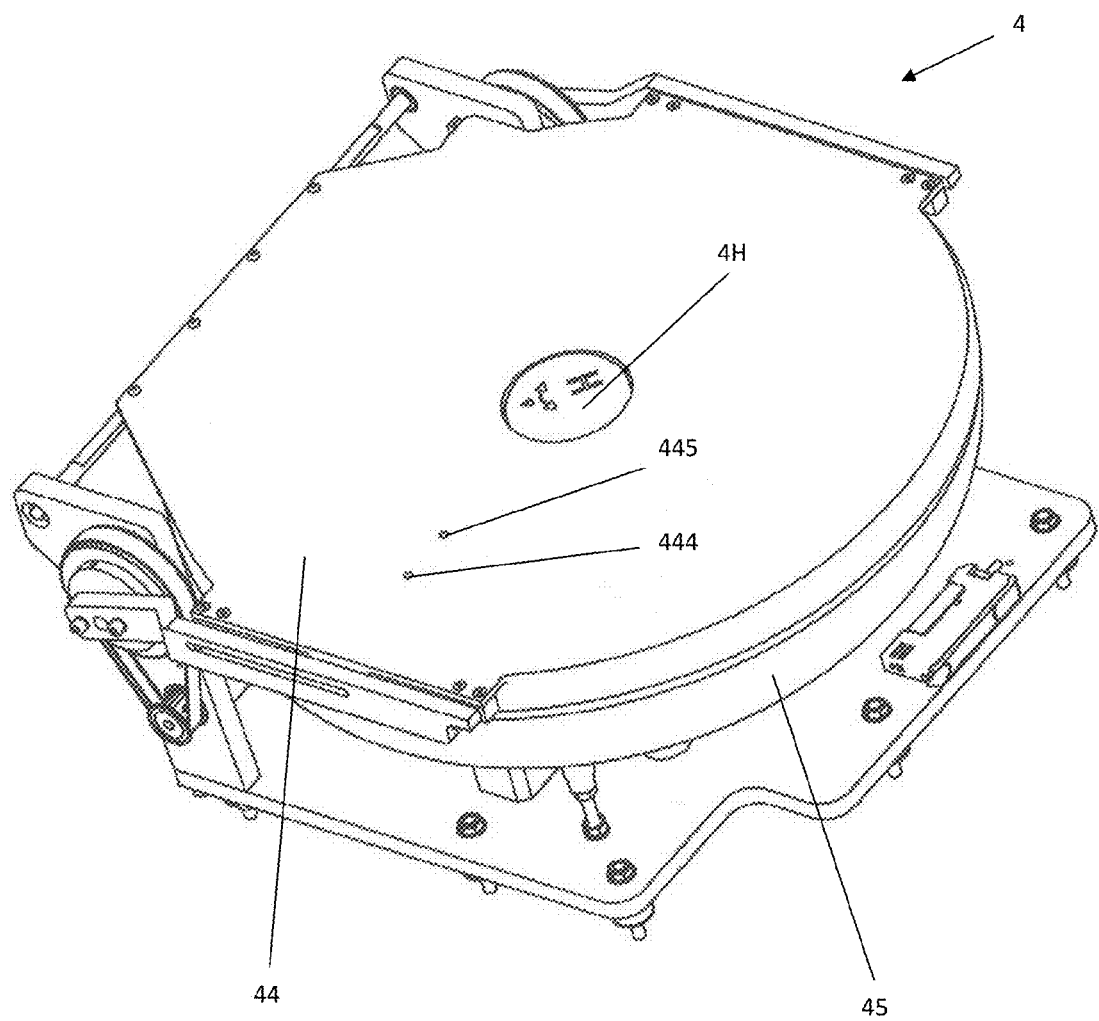

In a further embodiment, as shown in FIG. 5C-5D, the lid can be provided with at least one hole 444 (and 445) being adapted for and substantially small, but only big enough, for a needle to come therethrough. This will allow the needle or syringe arrangement 71 (with the help of the robot arrangement 7 and the computer means 8) to be able to add, through a dosing or dose hole 444, to at least one of the cell samples within a daughter sample container or test tube 3', that is(are) being pretreated or prepared, reagent(s), such as one antibody or at least two antibodies, cocktail(s), stabilizer(s), and even extra cells from a certain sample container or test tube 3 of the main test sample rack arrangement 2 corresponding to the sample cells in the respective daughter sample container or test tube 3' of the carousel/centrifuge arrangement 4, when the lid 44 is in a closed position. This adding process can also be done during the incubation and/or lysing in the dark. The dose hole 444 will also allow the needle or syringe arrangement 71 (with the help of the robot arrangement 7 and the computer means 8) to be able to take from the cell sample unnecessary and/or exceeding liquid that is to be drained or wasted. The small dosing hole 444 is placed on the lid 44 in such a way so that a desired daughter sample container or test tube 3' of the carousel/centrifuge arrangement 4 can be placed thereunder thus providing for carrying on of the adding process, and thereafter another desired daughter sample container or test tube 3' of the carousel/centrifuge arrangement 4 can be placed thereunder thus providing for carrying on of another adding process, and so on. In addition, another waste hole 445, shown in FIG. 5D, can be placed on the lid 44 in such a way so that an exceeding or unnecessary liquid wasting means 42 of the carousel/centrifuge arrangement 4 can be placed thereunder so that a needle or syringe of the needle or syringe arrangement 71 will be able to suck up unnecessary liquid, e.g. in case when the liquid wasting means 42 is not further connected to the waste station 95. All this is controlled by the computer means 8 and being executable with the help of needle or syringe arrangement 71 and the robot arrangement 7. The (x,y,z) coordinates and/or the positions of the small hole(s) 444, 445 can be preprogrammed and/or stored in the computer means 8. This second waste hole 445 will ease the function of the robot arm 72, because the arm 72 with the syringe arrangement 71 will then have a very short way to drain or waste into the liquid wasting means 42 unnecessary and/or exceeding liquid taken from the cell sample via the first dosing hole 444 and will not have to travel to the rinsing arrangement or station 10 in order to do so.

As shown in FIG. 5C-5D, the small hole(s) 444, 445 can have different positions on the lid 44 (see particularly the different placements of the dosing hole 444), and the coordinates and/or the positions thereof can be preprogrammed and/or stored in the computer means 8 so that the above-mentioned operations could be controlled by the computer means 8 and executed by the needle or syringe arrangement 71 and the robot arrangement 7 (the robot arm 72 therein). In an alternative embodiment, the dosing hole 444 can be concurrent with an initial position of a daughter sample container or test tube 3'.

In yet another embodiment of the invention, incubation and/or lysing in the dark can also be provided by having the housing or case 11 and lid or cover 111 of the entire system or instrument 1 made of non-transparent material, so that when the lid 111 is in a closed position with respect to the housing 11, both the lid 111 and the housing 11 of the instrument 1 will be arranged or adapted to thus provide for incubation and/or lysing (of the processed or (pre)treated cell samples) in the dark within the entire instrument 1. This means that light will not be allowed within the system or instrument 1 when the lid 111 is in a closed position with respect to the housing 11.

FIG. 8A-8D show different embodiments of an antibody/stabilizer container and cooler arrangement or means 6 according to the present invention. It is arranged for sustaining a desired temperature or temperature range therein and comprises a box-shaped housing 61 and a cover 62 having a number of holes 63 placed over a plurality of specially designed tubes or containers 3" for antibodies/stabilizers/reagents, or ready mixed cocktails, etc. and/or a number of bottles or containers, of at least one type, from at least one antibody fluid supplier, wherein each hole 63 is adapted for and is substantially small but big enough for a needle to come therethrough and further into the test tube or container 3" and/or supplier bottle or container thereunder in order to suck up liquid from the specially designed tube or container 3" or the supplier bottle or container without removing the cover 62, thus avoiding temperature changes, such as e.g. increase of temperature, within the antibody container and cooler arrangement 6. The desired temperature range within the antibody/stabilizer container and cooler arrangement or means 6 is from about 0.1° C. to about 15° C., and more particularly from about 1° C. to about 12° C., and even more particularly between about 2° C. and about 8° C. The antibody container and cooler arrangement 6 can further comprise at least two cartridges or cassettes 64, 65 for a plurality of specially designed tubes or containers 3" for antibodies/stabilizers/reagents, or ready mixed cocktails, etc. and/or for a number of bottles or containers, of at least one type, from at least one antibody fluid supplier. The plurality of specially designed tubes or containers 3" for antibodies/stabilizers/reagents, or ready mixed cocktails, etc. and/or the number of bottles or containers in each cartridge or cassette 64 or 65 can be practically or suitably arranged and chosen by the system 1 producer or supplier. In addition at least one of said cartridges or cassettes 64, 65 can be made detachable in order to be changed with another one having different arrangements and placements of the tubes or containers 3" and/or the supplier bottles or containers; which tube and/or supplier bottle arrangements and placements for each cartridge or cassette 64 or 65 can be preprogrammed in advance (by the system 1 producer or supplier and before initial use of the system or instrument 1), or alternatively, before initial cartridge or cassette use, they can be programmed or changed thereafter by the system user or maintenance responsible, as required or desired.

In an alternative embodiment each cartridge or cassette 64 or 65 can comprise an aluminum sleeve or casing for each specially designed tube or container 3" and/or supplier bottle or container in order to keep a substantially even temperature therein (thus avoiding big temperature differences between the fluid temperature at the top and at the bottom thereof). In yet another alternative embodiment, each supplier bottle or container in each cartridge or cassette 64 or 65 can be held therein slightly tilted, thus allowing for the needle of the needle or syringe arrangement or means 71 to be able to come through the bottle neck and be able to suck fluid from the bottom corner or edge of said supplier bottle or container.

For each cartridge or cassette 64 or 65 one contact indicating means 66 comprising at least two, and preferably at least three contact indicating devices for producing a "contact" or a "no-contact" signal, e.g. but not limited to reed contact means, can be arranged in the antibody container and cooler arrangement 6. The three contact indicating devices allow for nine different combinations for the cartridges or cassettes 64 or 65. Each cartridge or cassette 64 or 65 can have a certain combination of pins or contacts or reeds, so that when placed in the antibody container and cooler arrangement 6 the certain combination of pins or contacts or reeds on the certain cartridge or cassette 64 or 65 will get in contact with the contact indicating means 66 comprising contact indicating devices, and then a special signal (depending on the contact/pin/reed combination) will be produced by the contact indicating means 66 and sent the special signal to the computer means 8, so that said certain cartridge or cassette 64 or 65 will easily be recognized by the computer means 8 in the system 1. This means that the computer means 8 in the system 1 will know the exact place or placement (that has been preprogrammed) of each antibody/stabilizer/reagent, or ready mixed cocktail or the like in the certain cartridge or cassette 64 or 65 that has been placed in the antibody/stabilizer container and cooler arrangement or means 6. Alternatively, each contact indicating device can send its "contact" or "no-contact" signal to the computer means 8, and the computer means 8 will on the basis of these signals be able to recognize said certain cartridge or cassette 64 or 65.

In an alternative embodiment each cartridge or cassette 64 or 65 can comprise at least one guiding means 67, e.g. but not limited to a guiding pin, allowing for only one possible placement of the cartridge or cassette 64 or 65 into the antibody/stabilizer container and cooler arrangement or means 6, and not allowing the cartridge or cassette 64 or 65 to be turned e.g. 90 or 180 degrees and thereafter put into the antibody/stabilizer container and cooler arrangement or means 6 (incorrect positioning).

The antibody container and cooler arrangement 6 comprises a cooling means 68 comprising at least one inlet circulation fan 681 and at least one outlet circulation fan 682. Alternatively, the cooling means 68 can comprise at least one inlet circulation fan 681 or at least one outlet circulation fan 682, depending on the circulation needs and/or requirements. According to yet another embodiment, shown in FIG. 8D, the cooling means 68 can comprise two parallel inlet circulation fans 681 arranged or mounted beside each other on one side of the antibody container and cooler arrangement 6. The cooling means 68 can further comprise a heat sink 69 with a number of Peltier elements or heat sink elements (e.g., from one and above). In the embodiment shown in FIG. 8B, there are four such elements.

Additionally, each cartridge or cassette 64 or 65 can respectively comprise a handle 64H or 65H in order to be easily taken out from the antibody container and cooler arrangement 6.

According to an alternative embodiment of the invention, a part of the antibody container and cooler arrangement 6 and/or a part of one of said cartridges or cassettes 64, 65 can be insulated with suitable heat insulation (e.g. insulation plates) from the rest of the container and cooler arrangement 6. Said part thereof can comprise heating element(s) and temperature sensor(s) (not shown) being arranged to be able to sense and/or regulate the temperature (for said one or several sensors) and warm up (for said one or several heating elements) e.g. PBS and/or other liquid(s) to about 37° C. and/or over this temperature. Said part thereof can also comprise all necessary elements further needed for the above purpose (also discussed below in connection with another embodiment of said part, also called as heating part).

Figure 12:
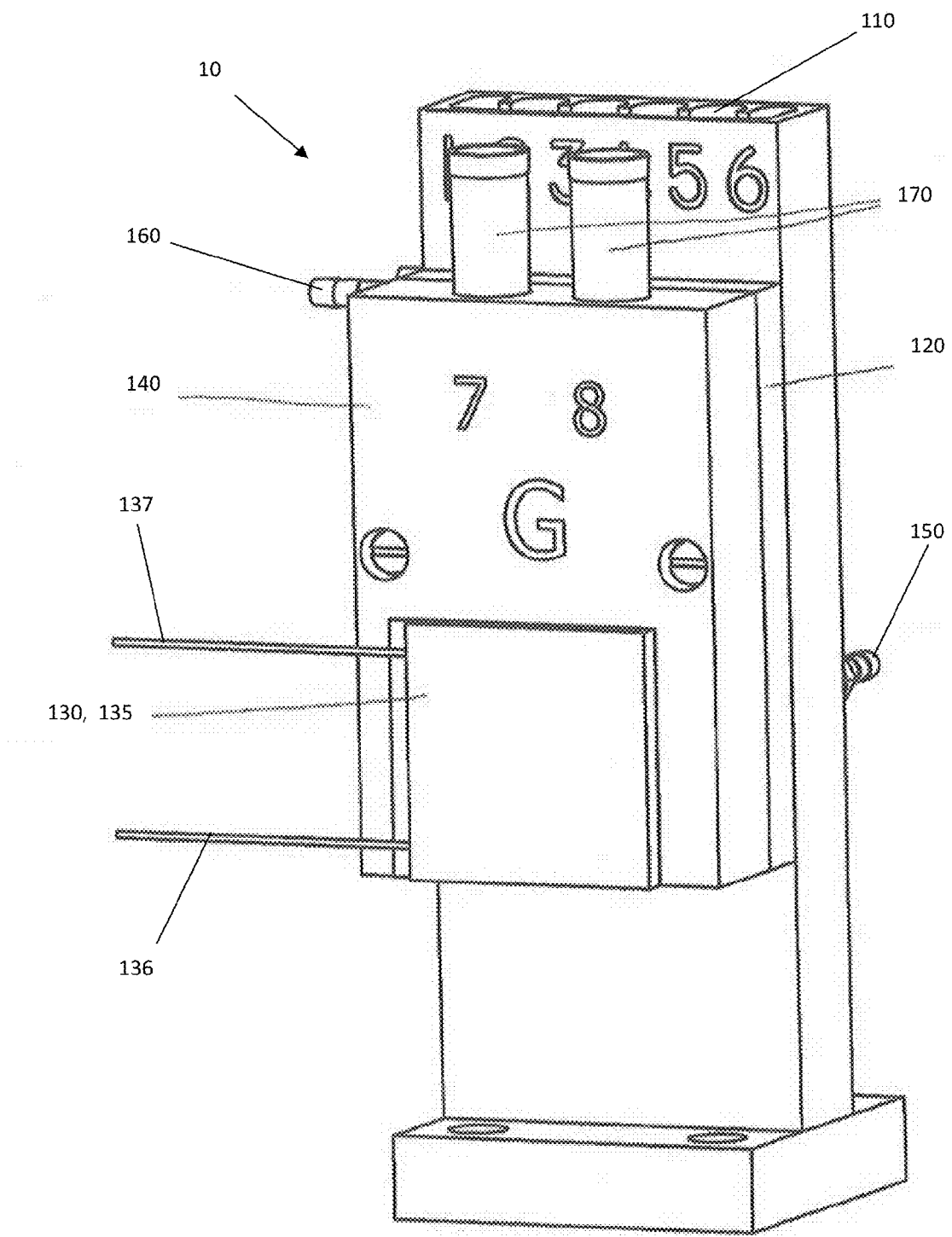
FIG. 12 shows a possible embodiment of a cleaning or rinsing arrangement or station with a determined heating part or station thereof.

Alternatively, heating or warming up of e.g. PBS and/or other liquid(s) can be done in the cleaning or rinsing arrangement or station 10, as shown in FIG. 12, wherein said predetermined number of chambers 110 (in this case: six) of the cleaning or rinsing arrangement or station 10, with the respective inlet 150 (connectable to the reagent rack arrangement or means or stations 12 for big volumes of reagent(s) and/or chemical(s) and/or rinsing or cleansing liquid(s) or solution(s), e.g. distilled water and/or cleansing product) and outlet 160 (connectable to the waste station 95) and possible pumping means 90 thereof, can be separated from the heating part of the rinsing station 10 with the help of an insulation plate 120. The heating part of the cleaning arrangement 10 can comprise a radiator 140 containing at least one 170 chamber or tube or holder or even compartment that can allow for a test tube to be placed therein (in this case: two) so that only the open top (side) can be visible, wherein e.g. PBS and/or other liquid(s) can be heated or warmed to about 37° C. and/or over this temperature by at least one heating element 130, such as but not limited to effect or power resistor(s) and/or Peltier element(s) and/or heat sink element(s). The warmed up liquid can thereafter be used for washing samples in the carousel/centrifuge arrangement 4 with respect to a certain protocol or procedure or operation that requires washing. A temperature sensor 135 can be adapted to sense and/or regulate the temperature, possibly with the help of the computer means 8. As it is evident from FIG. 12 there can be power 136 and/or signal 137 line(s) (in this solution and/or the previously mentioned alternative) being adapted respectively for supplying power to and/or control or regulation of said heating element(s) 130 as well as for communication(s) of input and/or output signals to and/or from the temperature sensor 135 that can be in contact with the computer means 8 for regulating or controlling of the temperature in the heating part of the cleaning or rinsing arrangement or station 10. As previously mentioned at least one specially designed tube or container 3" within the antibody container and cooler arrangement 6 can be used for keeping or holding a mixed cocktail. The cocktail(s) in said specially designed tube(s) or container(s) 3" can be readily made and/or can be prepared in the cocktail mixer means in the system or instrument 1.

In one embodiment, the cocktail mixer means can for example, be at least one dedicated tube or container 3" within the antibody container and cooler arrangement 6, and the cocktail can be prepared by adding or putting all needed ingredients into said at least one dedicated tube or container 3", wherein the needed ingredients can be taken from other tubes or containers 3" within the antibody container and cooler arrangement 6 and/or possibly from the reagent rack arrangement 12 (e.g., possibly via a certain chamber of the cleaning or rinsing arrangement or station 10) with the help of the needle or syringe arrangement 71 and the robot arrangement 7 (the robot arm 72 therein), and the mixing itself can be done by the needle or syringe arrangement 71, wherein the content or mixture within the dedicated tube or container 3" can be sucked up into said at least one syringe 73S, 73L of the needle or syringe arrangement 71 and then poured back into the dedicated tube or container 3" at least one time, and preferably several times, thus providing for good mixing of all ingredients within the dedicated tube or container 3". It is also possible to thereafter move the prepared cocktail into another tube or container 3" of the antibody container and cooler arrangement 6 that is acquired for cocktails, and the cocktail and its placement or position within the antibody container and cooler arrangement 6 can be stored in the computer means 8 for later use. One alternative possibility is to throw away or waste the cocktail (into the waste station 95, e.g. via a certain chamber of the cleaning or rinsing arrangement or station 10) after the preparation of the cell samples is completed, and the dedicated tube or container 3" can thereafter be cleaned or rinsed with the help of the needle or syringe arrangement 71 and the robot arrangement 7 (the robot arm 72 therein).

All tubes, bottles and containers can be made of glass, plastics or another suitable for the purpose material.

In one embodiment of the invention the reagent or antibody containers 3" can be designed to have a pointed bottom, so that remaining small volumes can easily be sucked or pumped out therefrom by the needle or syringe arrangement or means 71. In addition a small volume of an expired reagent or antibody or mixture/cocktail or the like in a certain reagent or antibody container 3" can for example be sucked or pumped out therefrom by the needle or syringe arrangement or means 71, and thereafter the needle or syringe arrangement or means 71 can optionally wash or rinse said certain reagent or antibody container 3" with the help of the needle or syringe arrangement or means 71. Finally, fresh reagent or antibody can be filled into said certain container 3". Alternatively, the certain reagent or antibody container 3" and/or supplier bottle or container, containing an expired reagent or antibody or the like, can be replaced by a new one containing fresh reagent or antibody or the like. Alternatively, since the computer means 8 is keeping track of all fluids/liquids in the system 1, a certain reagent or antibody container 3" and/or supplier bottle or container containing a small remaining volume of reagent or antibody or mixture/cocktail or the like, that is to expire soon, can be filled up with respective fresh reagent or antibody or mixture/cocktail or the like, and the new expiration date would be remembered by the storage or memory means in the computer means 8.

The system or instrument 1 can further comprise a cell density detection means for detecting and/or measuring the cell density of the cells in a certain main or mother test tube or sample container 3 e.g. in order to calculate and/or estimate, with the help of the computer means 8, the reagent or antibody fluid volume/amount needed to be added, and/or whether it is necessary to adjust or correct the reagent or antibody fluid volume/amount, and/or whether it is necessary to dispense more blood from the source or mother test tube or sample container 3 placed in the main test sample rack arrangement 2. The cell density detection means can comprise: a) an optical fiber means comprising a light source or emitter and arranged to send or emit light through a suitable plate or slide (having thereon the cells), e.g. a thin transparent glass or plastic plate or slide, or a suitable container (containing therein the cells), e.g. the daughter test tube 3' or one of the syringes from the needle or syringe arrangement or means 71 (e.g. the one 73S for small volumes, shown in FIG. 9), being able to hold thereon or contain therein the cells to be examined by the cell density detection means; and b) a light receiving or detection means arranged on the opposite side or end and adapted to receive the emitted light for further processing and/or estimating (via analog signal measurement, e.g. with the help of an analog signal amplifier) with the help of the computer means 8. The cell density detection means can further be mounted on the robot arrangement or means 7 in order to be able to be moved in all directions within the x,y,z or 3D area or space of the system or instrument 1. If a thin glass or plastic plate or slide is to be used for the above process, the system 1 can comprise a storage or stack/pile of several disposable plates or slides.

The system or instrument 1 can further comprise a fluid level measuring means for measuring and/or controlling/checking, with the help of the computer means 8, of the current fluid level in a container or chamber, etc. arranged in at least one of the following: the antibody and cooler arrangement 6; possibly/optionally the reagent rack arrangement 12 with said at least one bottle 13; possibly/optionally the cleansing or rinsing arrangement 10; and possibly/optionally the main test sample rack arrangement 2. The fluid level measuring means can be arranged in an electronic circuit with at least one of the needle(s) of the needle or syringe arrangement or means 71, wherein the electronic circuit can register when the needle tip touches the fluid surface in the container or chamber that is to be checked. Based on the liquid or fluid height from the bottom of the container or chamber to the fluid surface therein and in the vertical or z axis direction, which fluid height can be defined by the needle tip, the remaining fluid volume or amount can be calculated with the help of the computer means 8 and the container or chamber shape/form and/or capacity or volume information or data assigned to or connected with the predetermined position of this container or chamber, wherein the information or data can be stored or registered in the computer means 8, and particularly in its storage or memory means.

The current level in said at least one bottle 13 of the reagent rack arrangement 12 and/or in said at least one waste bottle or chamber or container 95 of the waste station 95 can be controlled or checked visually by the lab assistant or operator. Alternatively, for the reagent rack arrangement 12 and/or the waste station 95 at least one level monitoring means can be arranged, wherein the level monitoring means can comprise at least one sensor placed on or within the respective bottle or container adapted for detecting a certain level, e.g. one minimum and/or one maximum level. Several different known techniques can be chosen for use in this process.

The computer means 8 can be programmed to control and/or measure the fluid volumes, e.g. the antibody volumes, at e.g. start-up of the system/instrument 1 and/or at or with any predetermined of time interval or period.

If a refill in a certain antibody or reagent container or the like is needed the lab assistant or operator can be warned, e.g. by visual and/or audio warning message produced by the computer means 8 of the system/instrument 1, and/or by a wired and/or wireless message sent to a communicating with the system external device, e.g. an external PC or tablet or notebook or cell phone, etc.

In addition the robot arrangement or means 7, and particularly its arm arrangement 7, 72, can be steered by the computer means 8 to be correctly placed so that it would be able to show or point the exact container or chamber that is to be refilled or changed (e.g. due to expiration date) by means of at least one of: one of the needle(s); a pointer means (e.g. a kind of an arrow, physical or applied/painted e.g. on one wall or side of the robot arrangement 7); and a pointing light beam produced by a LED or light source that can be mounted on the robot arrangement or means 7, and particularly on its arm arrangement 7, 72. Thus any possibility of making a mistake, when the lab assistant or operator executes the required operation, is minimized or omitted.

Figure 10:
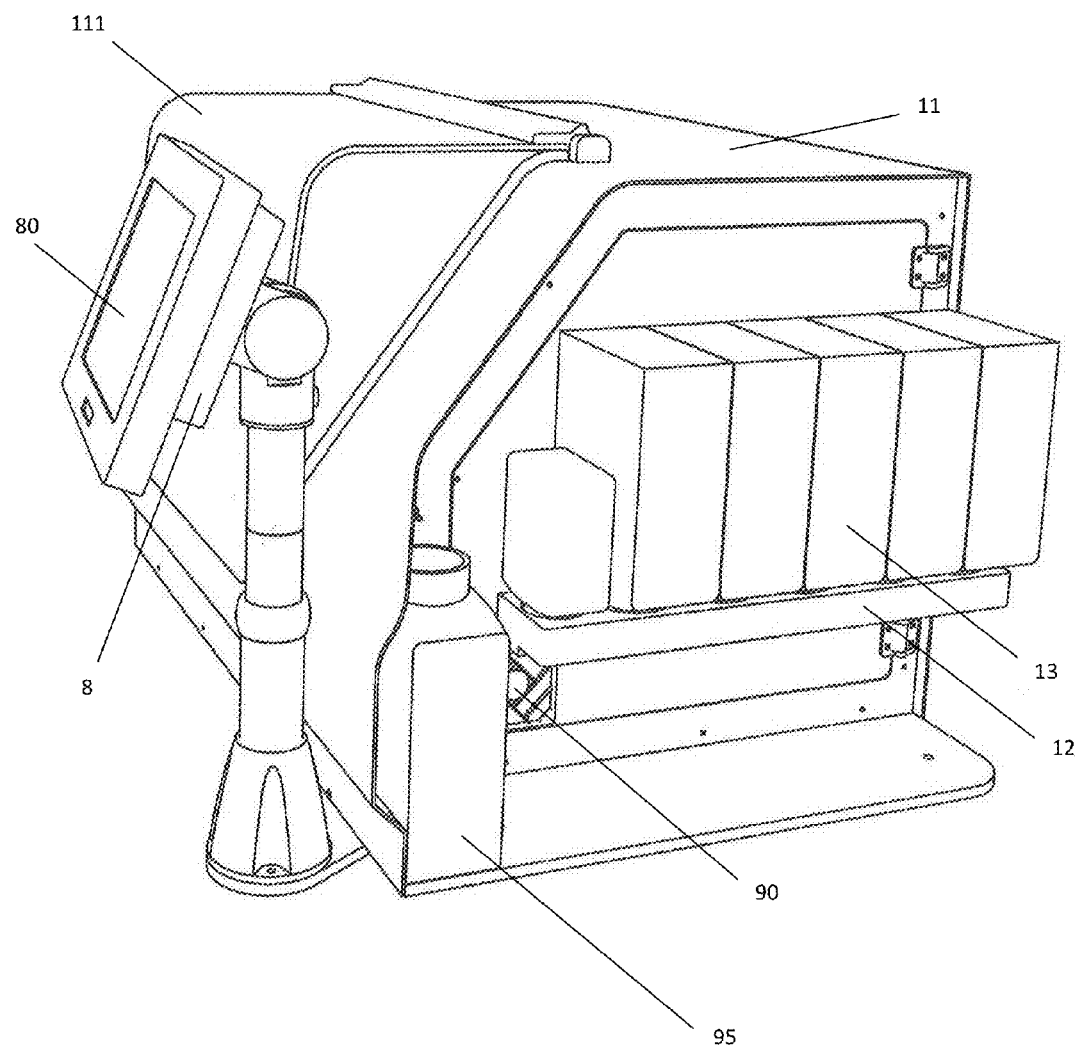
FIG. 10 shows one embodiment of a waste station with indicated pumping means and a reagent rack arrangement or means.

It is also possible to use T-coupling(s) in the system's hose or pipe arrangement means connecting or coupling different container(s) and/or chamber(s) therein in order to connect together the rinsing or rinse arrangement or station 10 and the exceeding liquid means 42 of the carousel/centrifuge arrangement or means 4 further with the waste station 95, e.g. possibly via the pumping means 90 (shown in FIG. 10).

FIG. 9A-9B show in detail embodiments of a needle or syringe arrangement or means the according to the present invention. As mentioned before, said at least one needle or syringe arrangement or means 71 can be arranged on one arm 72 of the robot arrangement or means 7 and can comprise at least one syringe 73S, 73L having a plunger 75 and a needle or cannula 74. The plunger 75 can be operated, e.g. pushed up or down, by at least one motor driven mechanism 76. In one embodiment the needle or syringe arrangement or means 71 can comprise two syringes 73S, 73L placed substantially vertically and parallel with each other and operated by said at least one motor driven mechanism 76. In another embodiment each syringe 73S, 73L can be operated independently by its own motor driven mechanism 76. According to one embodiment, the cell density detection means 77 can be arranged together with or within the needle or syringe arrangement or means 71 and can comprise an optical fiber means 78 arranged to send or emit light through the syringe 73S for small volumes, and a light receiving or detection means 79 arranged on the opposite side or end thereof and adapted to receive the emitted light for further processing and/or estimating of the cell density. Furthermore, in case when two needles or cannulas 74 are being used, i.e. one for each syringe arrangement 73S, 73L of the needle or syringe arrangement or means 71, said needle or syringe arrangement or means 71 together with said at least one motor driven mechanism 76 can be adapted, e.g. with the help of a common transmission belt 761 connected thereto, to be able to synchronize the two needles or cannulas 74, so that when the first one (e.g. the needle of the syringe arrangement 73S for small liquid volumes) is going down the other or second one (e.g. the cannula of the syringe arrangement 73L for large liquid volumes) will be going up. This is shown in FIG. 9B. The same can also apply for the plungers 75 of said needle or syringe arrangement or means 71.

Theory of Operation of the Instrument or System

1) Running a Protocol (Series of Activities or Actions)

Figure 11A:
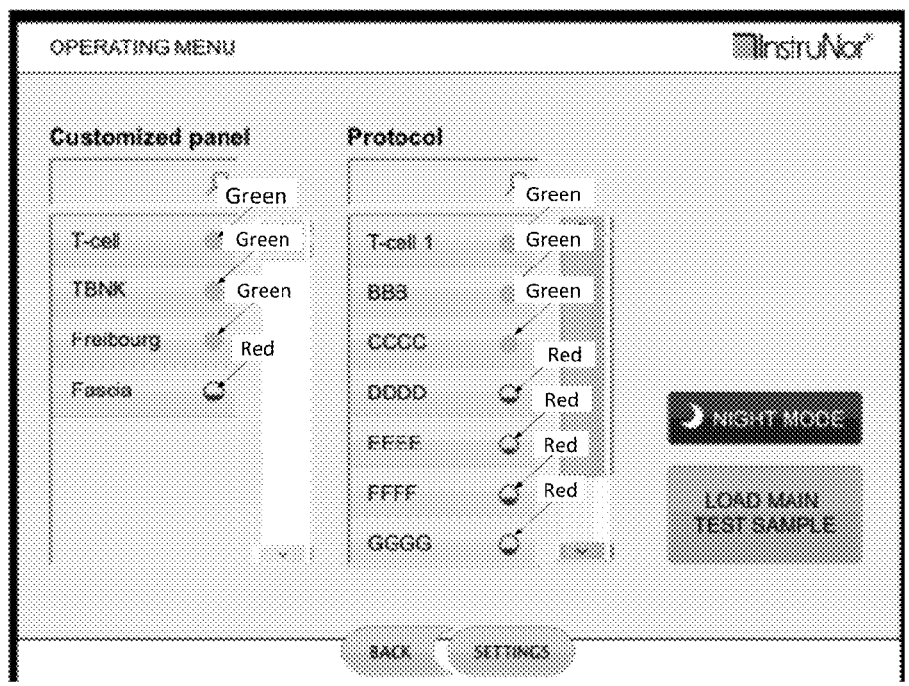
FIG. 11A-11P show screenshots of an exemplary operational procedure of the system according to the present invention.
Figure 11B:
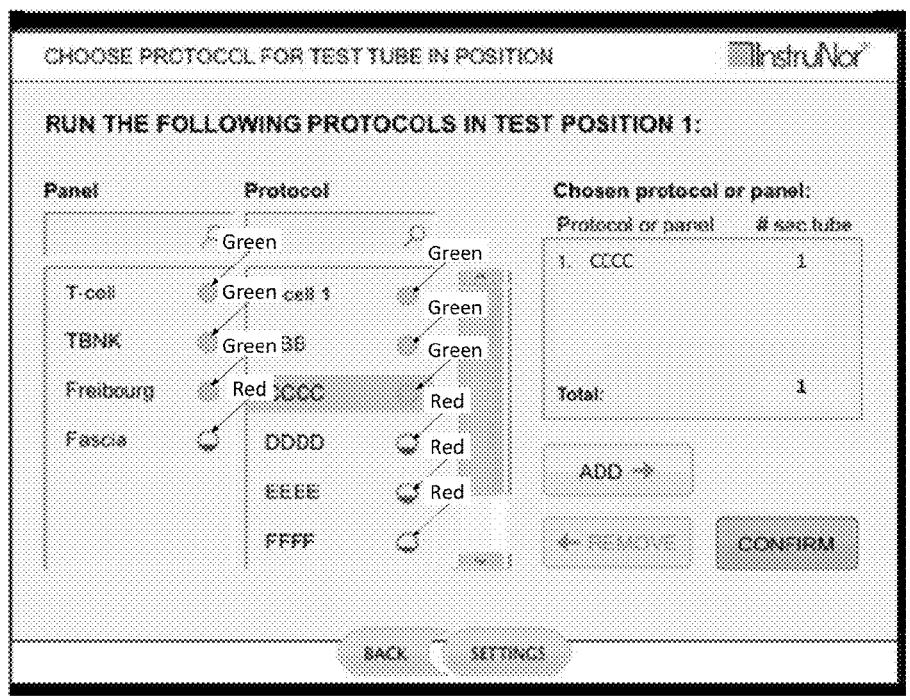
Figure 11C:
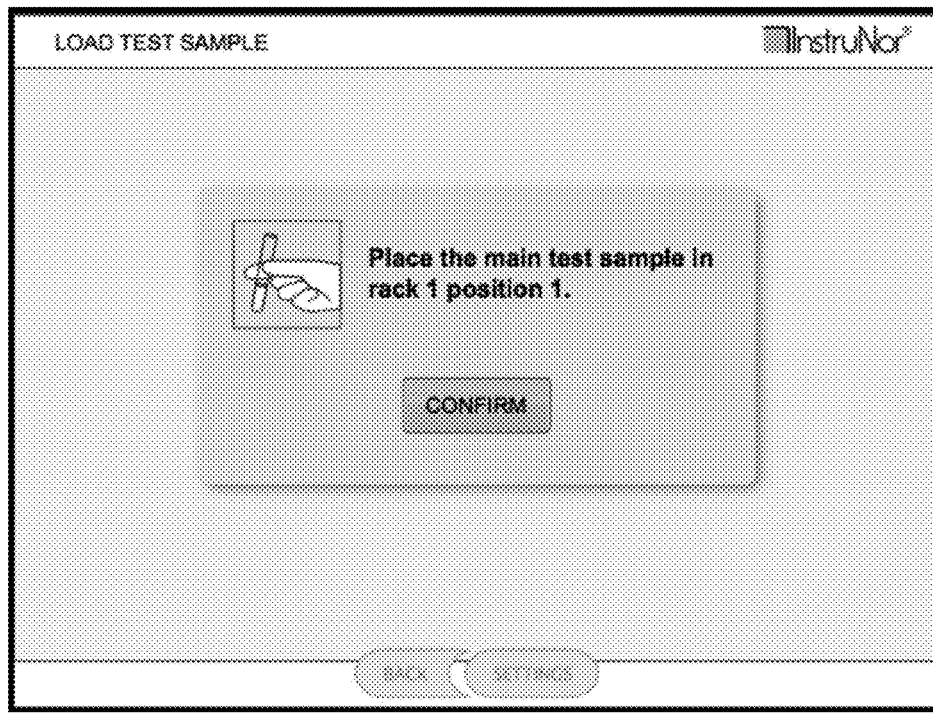
Figure 11D:
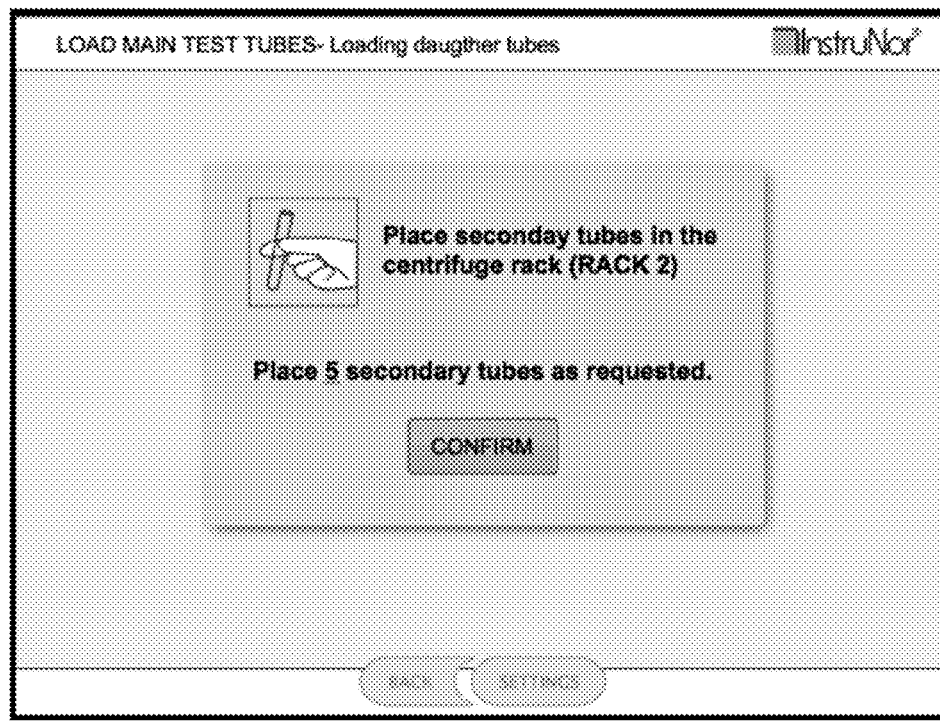
Figure 11E:
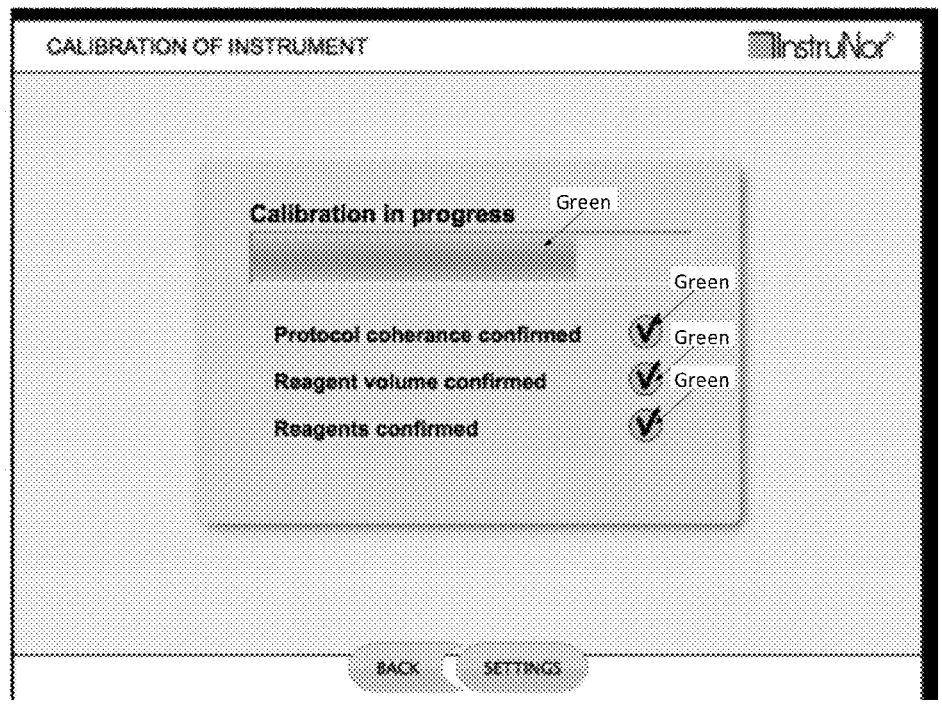
Figure 11F:
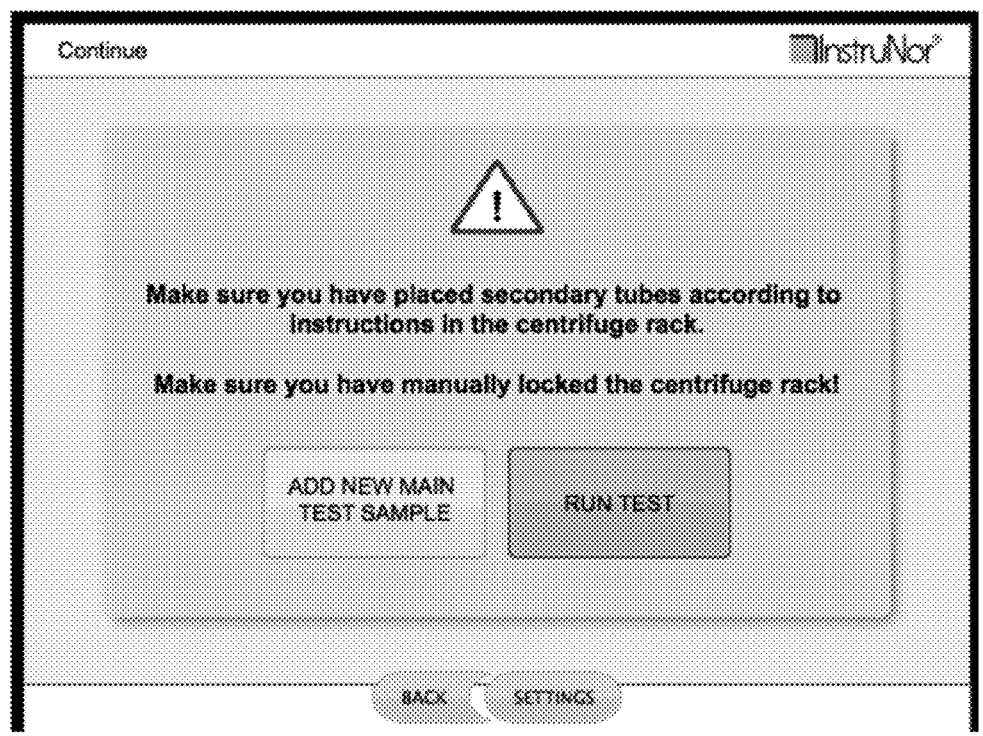
Figure 11G:
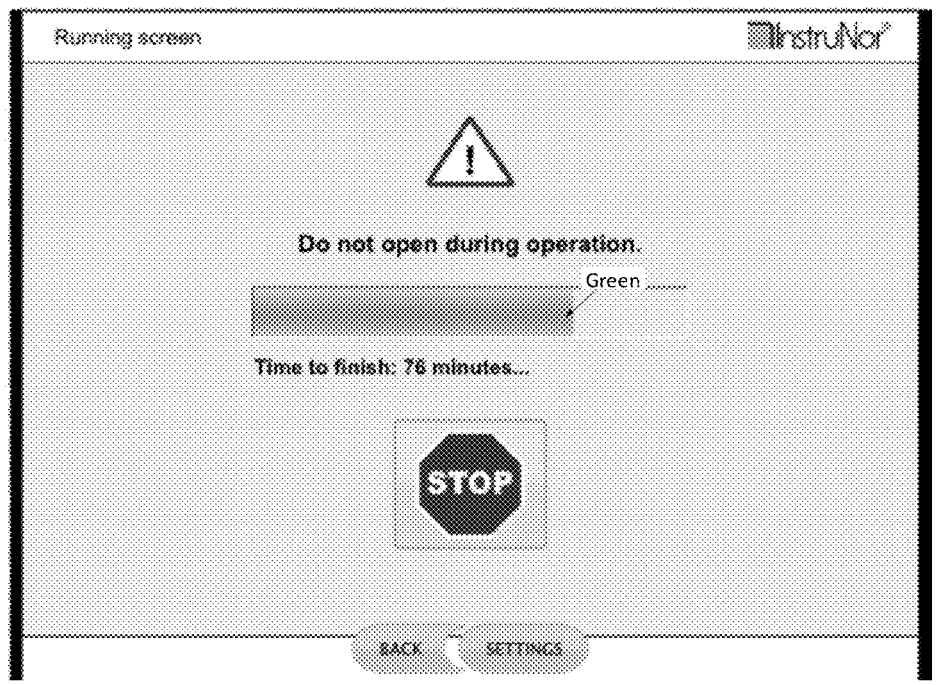
Figure 11H:
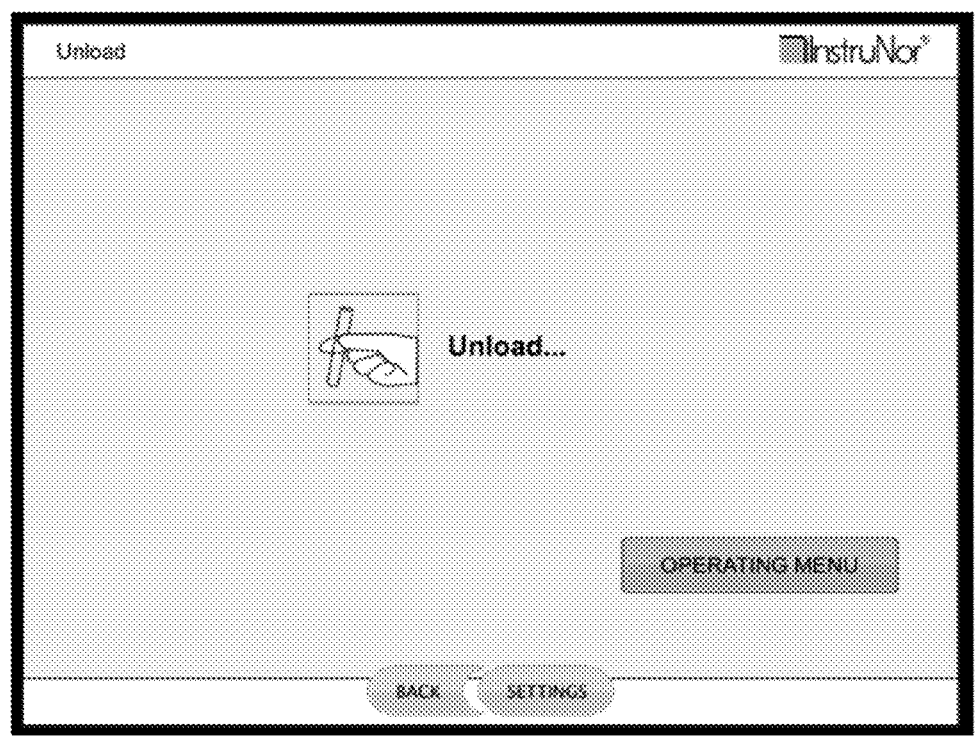
Figure 11I:
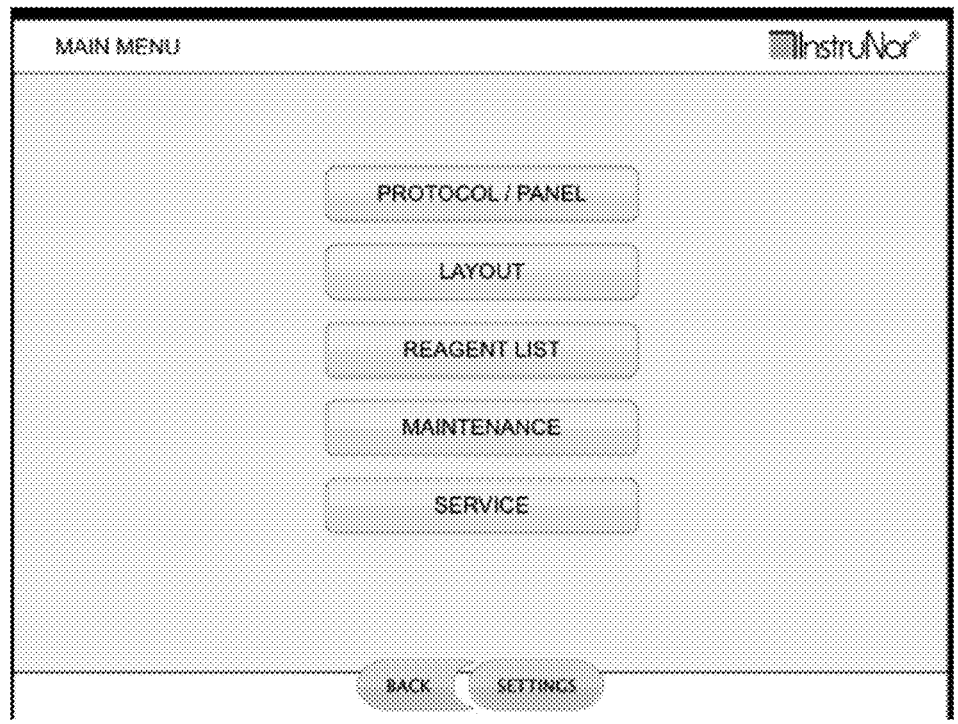
Figure 11J:
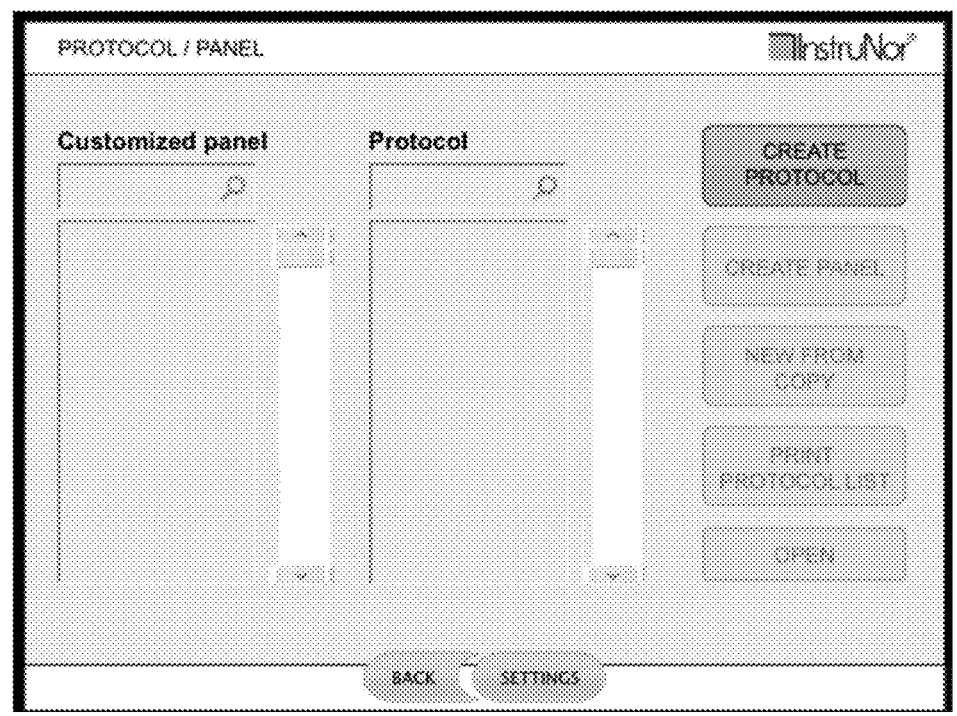
Figure 11K:
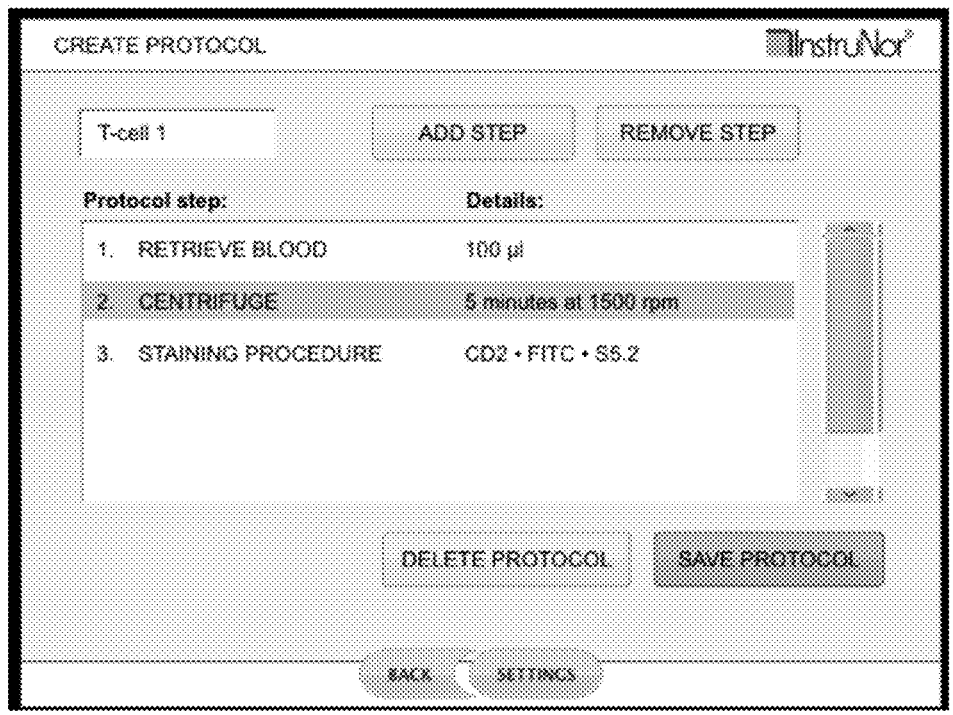
Figure 11L:
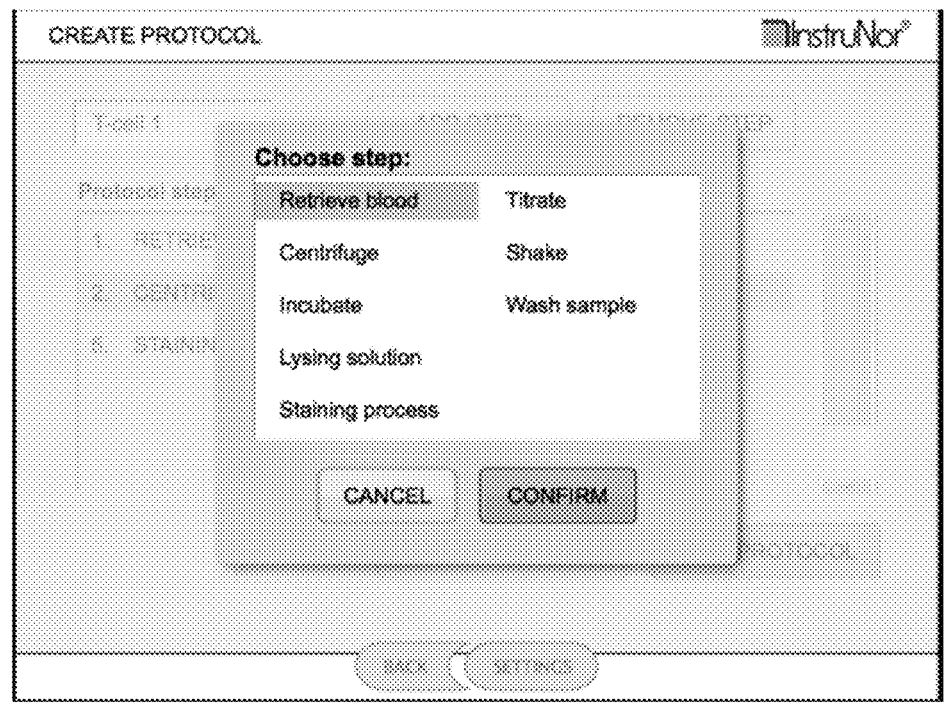
Figure 11M:
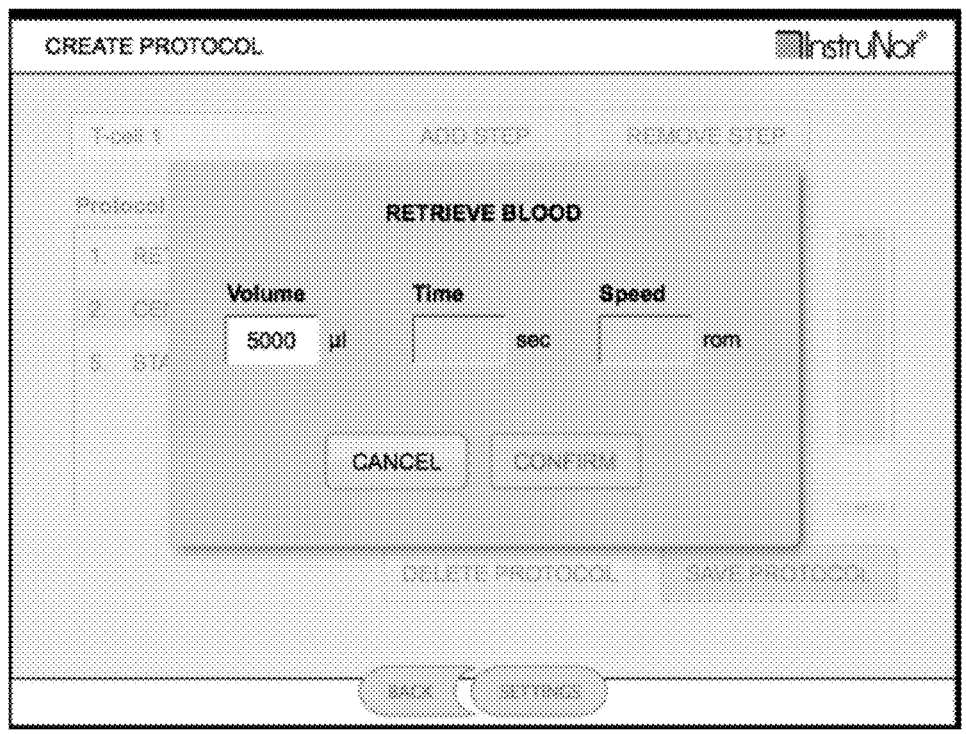
Figure 11N:
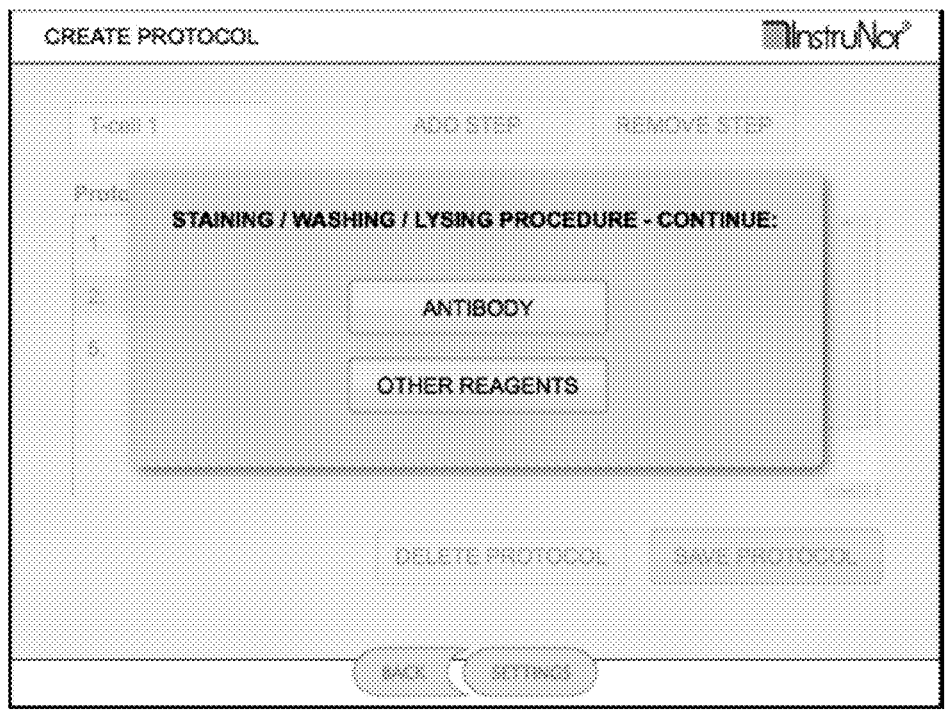
Figure 11O:
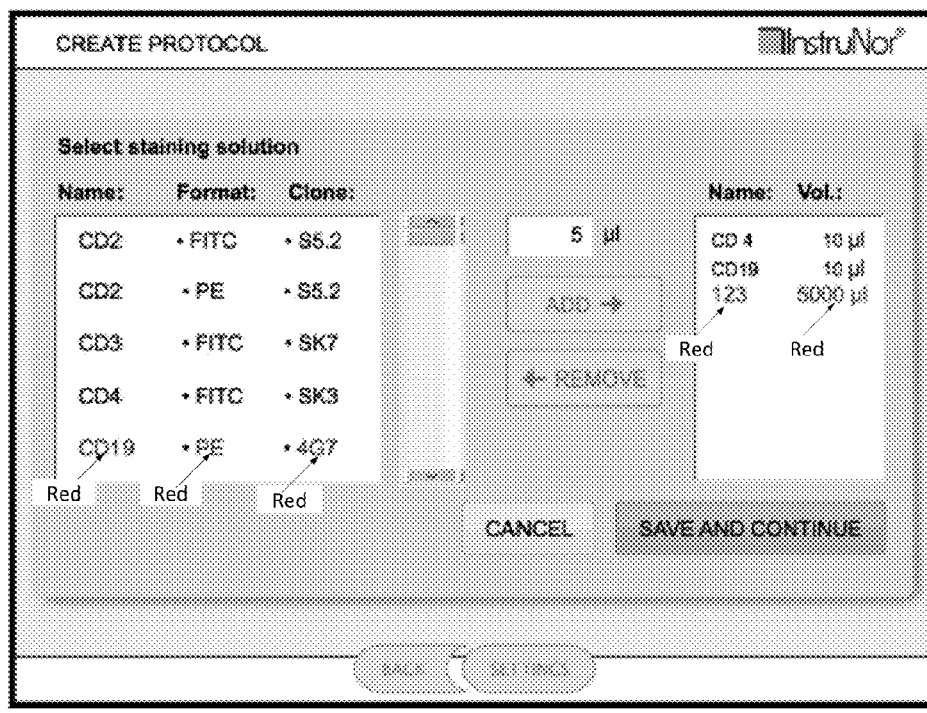
Figure 11P:
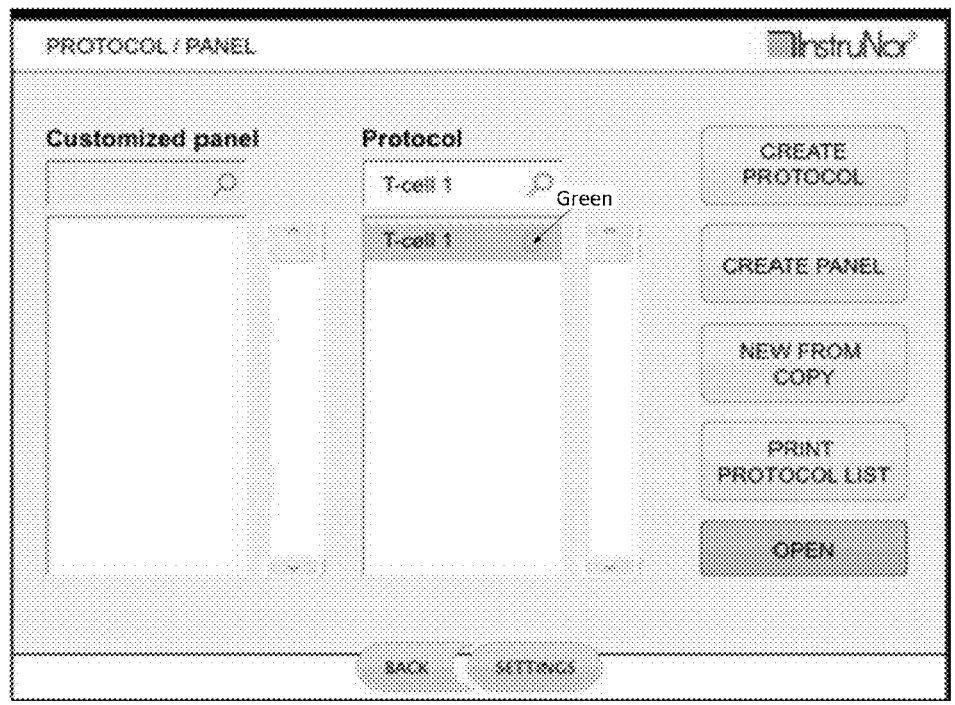

One standard example: The preparation procedure in the so called FlowStainer can have the following steps in e.g. an Enumeration of CD4 (cluster of differentiation 4) levels in e.g. HIV-infected cultures at an immunology lab:

i) The lab assistant selects, e.g. on the touch screen 80, the test program that is to be run or executed (see graphical user interface in FIG. 11A-11P).

The FlowStainer can also provide for this step a bar code reader arrangement (not shown) to program tests in the instrument or system 1.

ii) The lab assistant places the liquid human cell sample tube(s) 3 in the mother sample rack or main test sample rack arrangement or means 2 (rack 1), further places a number of daughter test tubes 3' in the carousel/centrifuge arrangement 4 (rack 2) according to the machine's instructions depending on the programmed number of main test tubes 3 and the programmed test(s) to be performed, locks the main cover or door 111, and presses the <<RUN TEST>> button.

iii) Now the instrument/system 1 will automatically run through the rest of the steps. The cap or cork 30 on the test tube or sample container 3 is lifted up automatically (see FIGS. 3 and 4) and the robot arm arrangement 7, 72 uses e.g. syringe number one/73L of the needle or syringe arrangement 71, and dispenses e.g. about 100 μl of whole blood from the mother sample tube or container 3 into a daughter test tube or sample container 3' placed in the carousel/centrifuge arrangement 4 (rack 2) (see e.g. FIGS. 4 and 6).

In a wash procedure an optical light can be used to detect necessary buffer volume to add to the test sample. The optical light can detect low cell count which opens the possibility for the Flow Stainer to dispense more blood into the daughter test tube 3' if necessary. This also optimizes use of expensive antibody or antibodies in a test, and minimizes thus overuse or excessive and unnecessary use of the expensive antibody or antibodies.

Alternatively, the blood cell density measuring can be performed, using blood from the main test tube or sample container 3, before blood sample is added or put into at least one daughter test tube or sample container 3' thus giving the operator enough information and good control over the necessary amounts of antibodies, buffer reagents, etc. to be used for that certain blood sample.

iv) The needle is then cleansed in the rinse station 10, e.g. with distilled water or other suitable liquid(s) and/or chemical(s).

v) The robot arrangement 7 with the arm arrangement 72 then uses e.g. syringe number two/73S of the needle or syringe arrangement 71, and dispenses in the whole blood e.g. about 20 μl of CD4 reagent found in the antibody and cooler arrangement or means 6 (rack 3) (see FIG. 8A-8D). The needle is then rinsed with e.g. PBS liquid or a liquid similar to the cleansing product at the rinse station 10.

vi) While the CD4 reagent is added to the whole blood the titrating or shaking arrangement 51; 53 can gently vortex the test sample (see FIG. 6). An incubation time of e.g. approximately 15-45 minutes can then be allowed. This is done at e.g. room temperature (from about 20° C. to about 25° C.) and possibly in the dark. As previously mentioned the incubation and/or lysing in the dark can be provided by the housing 45 and lid 44 of the carousel/centrifuge arrangement 4 or by the housing 11 or lid 111 of the instrument 1.

vii) Then syringe number one/73L is used to add e.g. about 2 ml of lysing solution (placed in the reagent rack arrangement or means 12 (rack 4)) to the daughter tube 3' at e.g. room temperature, followed by centrifuging the test sample at e.g. about 1.500 rpm or more. An incubation period of about 10-12 minutes can follow, being possibly done in the dark and at e.g. room temperature. As previously mentioned the incubation and/or lysing in the dark can be provided by means of the housing 45 and lid 44 of the carousel/centrifuge arrangement 4 or by means of the housing 11 and lid 111 of the instrument 1. The needle is then taken to the rinse station 10 for cleansing, using at least one cleansing liquid, e.g. Coulter Clenz.

viii) The titrating arrangement 51; 53 can then pour out exceeding liquid into/at the waste station 42.

ix) The test is then washed with 1×PBS with e.g. about 0.1% azide, adding e.g. about 0.5 ml of e.g. about 1% paraformaldehyde, by using e.g. syringe number two/73S. This is also used as a carrier liquid that can fixate the cells ahead of going into the Flow Cytometer. The needle is then rinsed with e.g. distilled water at the rinse station 10.

x) The Flow Stainer now finishes the automated preparation procedure and send out an alert signal as well as it gives visible information (see also FIG. 11H) on the touch screen 80 to unload the instrument or system 1. The daughter test tube 3' can now be directly transmitted into the Flow Cytometer for complete analysis.

2) Running the Test on the Instrument Touch Screen

The abovementioned exemplary test is easy to run on a ready-to-run programmed FlowStainer instrument or system 1 according to the present invention. The following steps are required to run this exemplary test:

FIG. 11A shows a screenshot of the Operating Menu.

When a FlowStainer instrument or system 1 is at "Operating mode", the Operating Menu (FIG. 11A) is the screenshot that will be default at any time. The software product has a number of already programmed protocols and panels (multiple protocols) that are easy to access at any time.

i) When the lab engineer/assistant is ready to run a test, he/she checks that the preferred protocol is "green" (e.g., "T-cell 1", "BBB", "CCCC" as shown in FIG. 11A) which means it's confirmed ready by the instrument or system 1. "Red" sign (e.g., "DDDD", "EEEE", "FFFF", "GGGG" as shown in FIG. 11A) means "not ready" or "not runnable" or "not executable", or the like.

ii) Press the <<Load Main Test Sample>> button.

FIG. 11B shows a screenshot of the procedure for choosing a protocol for test tube in position.

In the screen shown in FIG. 11B, the lab engineer or lab assistant selects what protocol or panel (multiple protocols) that is to be run or executed. All protocols or panels are programmed in the Main Menu in advance. If no protocols or panels are programmed in advance, there will not be any to choose from in this screen.

iii) The protocol or panel is chosen by pressing on the text line and then pressing the <<CONFIRM>> button. If the protocol or panel is chosen and an additional protocol is needed, press <<PROTOCOL NAME>> and <<ADD>>, then choose or select an additional protocol and finally press <<CONFIRM>>. In the upper right box there is also shown some information on how many secondary daughter test tubes 3' have to be placed in the carousel/centrifuge arrangement 4.

iv) When done, press the <<CONFIRM>> button.

FIG. 11C shows a screenshot of the procedure for loading main test tube(s).

v) An immediate pop-up asks for a liquid human cell sample in the main test sample rack arrangement or means 2 (rack 1). At the same time the main door seal 111 is opened. When a sample tube 3 is placed in position, press the <<CONFIRM>> button.

FIG. 11D shows a screenshot of the procedure for loading daughter test tube(s).

vi) The number of daughter or secondary test tubes 3', that are requested to be placed in the carousel/centrifuge rack arrangement 4, is indicated on the screen shown in FIG. 11D. The requested daughter or secondary test tubes 3' are put or placed or inserted one by one in the carousel/centrifuge rack arrangement or means 4, and the inserted tube is detected by means of a suitable detection or sensor device e.g. in order for next tube to be inserted, alternatively or additionally followed by pressing the <<CONFIRM>> button. The Main Cover/Door 111 must then be closed.

FIG. 11E shows a screenshot of the procedure for calibration of the instrument.

vii) A calibration procedure is now initiated in order to find out that the instrument is ready to run the test without errors.

FIG. 11F shows a screenshot of the Continue procedure or step.

viii) When the calibration is done and found approved, the instrument or system 1 will automatically proceed to the next step. A choice to add more test samples 3 is now given, as well as the <<RUN TEST>> option/button.

FIG. 11G shows a screenshot of the Running screen process.

ix) When <<RUN TEST>> is pressed in the screenshot shown in FIG. 11F, the running screen gives real time, updated information on the operation progress.

FIG. 11H shows a screenshot of the Unload step.

x) When the screenshot shown in FIG. 11H is visible on the touch screen 80, the main cover 111 is unlocked and it is now possible to remove the test sample(s) and the main sample(s) from the racks. The daughter tube(s) 3' is(are) now ready to go directly into the Flow Cytometer for further analysis.

3) Programming the Protocol on the Instrument Touch Screen

In order to be able to run tests in the Flow Stainer instrument 1 there are a number of preprogramming activities to perform in addition to filling of reagents/antibodies in the bottle rack (rack 4) and the antibody rack (rack 3).

The programming of protocols and panels is done the following way on the touch screen (start out on the Operating Menu as shown in FIG. 11A):

i) In order to be able to program the system press the <<SETTINGS>> button in the bottom part of the screen 80.

FIG. 11I shows a screenshot of the Main Menu.

ii) The <<PROTOCOL/PANEL>> button leads to the create page for programming a protocol.

FIG. 11J shows a screenshot of the Protocol/Panel window.

iii) If no protocols or panels are preprogrammed then the boxes therein will be empty. Press the <<CREATE PROTOCOL>> button.

FIG. 11K shows a screenshot of the protocol creating procedure (Create Protocol).

iv) Initially the Create Protocol page can be empty. In order to program a protocol a name is written in the top left box. By using <<ADD STEP>> each and every step in the protocol can be programmed.

FIG. 11L shows a screenshot of the step choosing procedure of the protocol creating procedure (Create Protocol—Choose step)

v) All "activities" or "steps" that the instrument or system 1 can handle are activated by pressing the text line and then the <<CONFIRM>> button.

FIG. 11M shows a screenshot of the Volume/Time/Speed input procedure within the step choosing procedure of the protocol creating procedure.

vi) For the following activities the Volume/Time/Speed pop-up is automatically received when programming a protocol: Retrieve blood, Centrifuge, Incubate, Vibrate, Titrate, and Shake.

FIG. 11N shows a screenshot of the Staining/Washing/Lysing input procedure within the step choosing procedure of the protocol creating procedure, wherein antibodies or other reagents can be chosen and regulated, etc.

vii) For the following activities the Staining/Washing/Lysing pop-up is automatically received when programming a protocol: Staining process, Wash sample, and Lysing solution.

FIG. 11O shows a screenshot of the procedure for selection staining solution(s) (Create protocol—Select staining solution).

xiii) When pressing <<Antibody>> or <<Other reagents>> (as shown in FIG. 11N) the Select staining solution window opens up. The difference between the two views is how the list of antibodies/reagents is sorted. Based on the antibody/reagent ID in the left box, shown in FIG. 11O, the staining solution is selected. By pressing the button called <<SAVE AND CONTINUE>>, the system will return to the screenshot "Create Protocol", shown in FIG. 11K, in order to add more steps in the protocol program.

ix) When the protocol is completed, pressing the <<SAVE PROTOCOL>> button will finalize the programming.

FIG. 11P shows a screenshot of the Protocol/Panel window which is similar to the one shown in FIG. 11J, but having the new programmed protocol (called e.g. T-cell 1) visible on the screen.

x) The new programmed protocol is now visible in the Protocol/Panel screen or window. Select the <<SETTINGS>> button in order to return to Main Menu. The new programmed protocol, T-cell 1, is now possible to choose in the screenshot, shown in FIG. 11B, regarding the procedure for choosing a protocol for test tube in position (Choose Protocol for Test Tube in Position).

As it can also be seen in FIG. 11P, there are other operations that can be executed, such as: printing a protocol list (Print Protocol List), creating a new protocol (Create Protocol), etc.

Additional steps or operations, e.g. as described outside the "Theory of Operation of the Instrument or System" section herein, connected to the operational, maintenance and programming functions of the system can also be programmed in the software product and run or performed on the system or instrument.

Additional modifications, alterations and adaptations of the present invention will suggest themselves to those skilled in the art without departing from the scope of the invention as expressed and stated in the following patent claims.

The invention claimed is:

1. A fully automated cell pretreating process instrument for preparing at least one cell sample ahead of flow cytometry analysis, the instrument being encapsulated in an instrument housing, the instrument housing comprising:
    a main test sample rack arrangement for a number of sample containers;
    a centrifuge arrangement comprising a centrifuge housing, the centrifuge housing comprising a carousel, the carousel comprising a number of secondary sample container holders;
    a container and cooler arrangement for a number of test tubes or containers, wherein the container and cooler arrangement provides for sustaining a desired temperature range therein;
    a robot arrangement comprising at least one arm arrangement for taking cell samples from the main test sample rack arrangement and putting the cell samples in the centrifuge arrangement; and
    a component control and operating computer comprising at least one CPU configured to control the main test sample rack arrangement, the centrifuge arrangement, the container and cooler arrangement, and the robot arrangement so as to achieve full automation of an entire cell pretreating process,
    wherein the centrifuge arrangement comprises a motor drive releasably in engagement with the carousel, the secondary sample container holders are pivotably hinged to the carousel so as to provide a "swinging bucket motion" principle, and the centrifuge arrangement further comprises a motor driven titrating or shaking arrangement which includes a pitch rack or pinion operated by a motor driven gear wheel.

2. The instrument according to claim 1, further comprising a reagent rack arrangement arranged to accommodate one or more reagent bottles.

3. The instrument according to claim 1, wherein the main test sample rack arrangement comprises a cap remover for automated removing of and/or putting on one or more sample container caps.

4. The instrument according to claim 1, wherein the main test sample rack arrangement comprises an additional sample container holder for holding one or more sample containers of a different type.

5. The instrument according to claim 1, wherein the robot arrangement further comprises at least one needle or syringe arrangement comprising at least one needle or cannula and at least one syringe having a plunger, the plunger being driven by at least one motor driven mechanism included in the at least one needle or syringe arrangement.

6. The instrument according to claim 5, wherein the at least one needle or syringe arrangement comprises two syringes placed substantially vertically and parallel with each other, a first one of the two syringes is a microliter (µl) range syringe, and a second one of the two syringes is a milliliter (ml) range syringe.

7. The instrument according to claim 1, further comprising a cleansing or rinsing station, wherein the at least one syringe of the at least one needle or syringe arrangement is configured to be cleansed or rinsed with at least one cleansing or rinsing fluid or liquid or solution and/or chemical.

8. The instrument according to claim 1, further comprising a waste station having a pump and being adapted for collecting waste fluid(s), liquid(s), stabilizer(s), reagent(s), antibodies and/or sample(s).

9. The instrument according to claim 1, wherein the component control and operating computer comprises an output interface and an input interface.

10. The centrifuge arrangement according to claim 9, wherein the output interface and the input interface comprise at least one of a screen or display, a keyboard, and a keyset of button(s).

11. The instrument according to claim 1, wherein the component control and operating computer further comprises storage or memory.

12. The instrument according to claim 1, further comprising a communicator for wired and/or wireless and/or Bluetooth® communication with external devices.

13. The instrument according to claim 1, wherein the motor drive of the centrifuge arrangement is configured to allow for movement or centrifuging in a clockwise and/or a counterclockwise direction of the carousel.

14. The instrument according to claim 13, wherein the motor drive of the centrifuge arrangement is software controlled for centrifuging at different speeds.

15. The instrument according to claim 1, wherein the centrifuge housing is made of a light reductive and/or non-transparent material, the centrifuge housing further comprising a lid made of a light reductive and/or non-transparent material, and wherein, in a state in which the lid is in a closed position with respect to the centrifuge housing, both the lid and centrifuge housing are arranged to provide for incubation and/or lysing in dark and/or excluding damaging UV-rays of processed or pretreated cell samples.

16. The instrument according to claim 1, further comprising a cell density detector for detecting a cell density of cells in one of the test tubes or the sample containers.

17. The instrument according to claim 16, wherein the cell density detector comprises an optical fiber arranged to send or emit light through cells on or within a transparent plate or container, and a light receiver or detector arranged on an opposite side or end thereof and adapted to receive the emitted light for further processing and/or estimating of the cell density.

18. The instrument according to claim 1, further comprising a hose or pipe arrangement connecting or coupling different container(s) and/or chamber(s) and/or bottle(s) together within the instrument housing.

19. The instrument according to claim 1, further comprising a fluid level measurer for measuring and/or controlling/checking a fluid level in a container or chamber arranged in at least one of the following:
    the container and cooler arrangement;
    a reagent rack arrangement;
    a cleansing or rinsing station; and
    the main test sample rack arrangement, wherein the fluid level measurer is arranged in an electronic circuit with at least one needle of a needle or syringe arrangement of the robot arrangement, in such a manner that the electronic circuit is configured to register when a tip of the at least one needle touches a fluid surface in the container or chamber, and, based on a liquid or fluid height from a bottom of the container or chamber to the fluid surface therein and in a vertical or z axis direction, a remaining fluid volume or amount is calculated.

20. The instrument according to claim 1, wherein the container and cooler arrangement comprises a housing and a cover, wherein the cover has a number of holes placed over a plurality of tubes or containers, and/or a number of bottles, wherein each of the holes is adapted for a needle to penetrate therethrough and further into one of the tubes or containers and/or bottles thereunder in order to suck up liquid therefrom without removing the cover.

21. The instrument according to claim 1, wherein the container and cooler arrangement further comprises a cooler comprising at least one inlet circulation fan, at least one outlet circulation fan, and a heat sink having a number of Peltier elements, for sustaining the desired temperature range therein.

22. The instrument according to claim 1, wherein the container and cooler arrangement further comprises at least two cartridges or cassettes for a plurality of tubes or containers, and/or for a number of bottles, wherein at least one of the at least two cartridges or cassettes is detachable.

23. The instrument according to claim 1, wherein the instrument housing further comprises a lid.

24. The instrument according to claim 1, wherein the pitch rack of the motor driven titrating and shaking arrangement, in an extreme position relative to the motor driven gear wheel, is in engagement with one of the secondary sample container holders and pivots the one of the sample container holders more than 90° from a vertical position to a position above horizontal.

25. The instrument according to claim 1, wherein the container and cooler arrangement further comprises a cooler comprising at least one inlet circulation fan.

26. The instrument according to claim 1, wherein the container and cooler arrangement further comprises a cooler comprising at least one outlet circulation fan.

27. The centrifuge arrangement according to claim 1, wherein the motor driven titrating and shaking arrangement is in engagement with the secondary sample container holders.

28. A centrifuge arrangement comprising:
a centrifuge housing, the centrifuge housing comprising a carousel, the carousel comprising a number of sample container holders;
a motor drive releasably in engagement with the carousel, the sample container holders being pivotably hinged to the carousel so as to provide a "swinging bucket motion" principle, and;
a motor driven titrating or shaking arrangement coupled to the motor drive, the motor driven titrating or shaking arrangement including a pitch rack or pinion operated by a motor driven gear wheel.

29. The centrifuge arrangement according to claim 28, wherein the motor drive is configured to allow for movement or centrifuging in a clockwise and/or a counterclockwise direction.

30. The centrifuge arrangement according to claim 29, wherein the motor drive is software controlled for centrifuging at different speeds.

31. The centrifuge arrangement according to claim 28, further comprising a lid made of a light reductive and/or non-transparent material.

32. The centrifuge arrangement according to claim 31, wherein the lid is motor driven.

33. The centrifuge arrangement according to claim 31, further comprising a locked confirmation sensor configured to indicate whether the lid is locked or open.

34. The centrifuge arrangement according to claim 31, wherein the lid comprises at least one dose hole.

35. The centrifuge arrangement according to claim 34, wherein the at least one dose hole corresponds vertically with a position of a test tube allowing a needle or syringe arrangement to be able to access the test tube through at the at least one dose hole.

36. The centrifuge arrangement according to claim 35, wherein the motor drive is configured to provide rotation of the carousel and thereby movement of the sample container holders with test tubes in a stepwise rotation which facilitates vertical alignment between the test tubes and the at least one dose hole in the lid.

37. The centrifuge arrangement according to claim 28, further comprising a cell density detector for detecting a cell density of cells in a main test tube or sample container.

38. The centrifuge arrangement according to claim 28, wherein the cell density detector comprises an optical fiber arranged to send or emit light through cells on or within a transparent plate or container, and a light receiver or detector arranged on an opposite side or end thereof and adapted to receive the emitted light for further processing and/or estimating of the cell density.

39. The centrifuge arrangement according to claim 28, wherein the pitch rack of the motor driven titrating and shaking arrangement, in an extreme position relative to the motor driven gear wheel, is in engagement with one of the sample container holders and pivots the one of the sample container holders more than 90° from a vertical position to a position above horizontal.

40. The centrifuge arrangement according to claim 28, wherein the motor driven titrating and shaking arrangement is in engagement with the sample container holders.

41. A non-transitory computer-readable medium encoded with computer-executable instructions for controlling the instrument according to claim 1, the computer-executable instructions comprising:
taking cell samples from the main test sample rack arrangement,
putting the cell samples in the centrifuge arrangement,
taking stabilizers or antibodies from the container and cooler arrangement,
adding the stabilizers or antibodies to the cell samples in the centrifuge arrangement, and
titrating or shaking the cell samples.

42. A software module configured to execute the computer-executable instructions encoded on the non-transitory computer-readable medium according to claim 41.

* * * * *